United States Patent
Reiser

(10) Patent No.: US 9,205,135 B2
(45) Date of Patent: Dec. 8, 2015

(54) PODOCYTE PH MODULATION AND USES THEREOF

(75) Inventor: Jochen Reiser, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 13/497,451

(22) PCT Filed: Sep. 22, 2010

(86) PCT No.: PCT/US2010/049777
§ 371 (c)(1), (2), (4) Date: May 8, 2012

(87) PCT Pub. No.: WO2011/037970
PCT Pub. Date: Mar. 31, 2011

(65) Prior Publication Data
US 2012/0219542 A1 Aug. 30, 2012

Related U.S. Application Data

(60) Provisional application No. 61/244,604, filed on Sep. 22, 2009.

(51) Int. Cl.
*A61K 31/198* (2006.01)
*A61K 38/48* (2006.01)
*G01N 33/50* (2006.01)

(52) U.S. Cl.
CPC ............ *A61K 38/4873* (2013.01); *A61K 31/198* (2013.01); *G01N 33/5044* (2013.01); *G01N 2800/34* (2013.01)

(58) Field of Classification Search
None
See application file for complete search history.

(56) References Cited

U.S. PATENT DOCUMENTS

2007/0197438 A1* 8/2007 Reiser et al. .................... 514/12
2007/0238790 A1 10/2007 Liu et al.

FOREIGN PATENT DOCUMENTS

WO WO/95/11019 * 4/1995 ............. A23L 1/305
WO WO 2011049777 A1 * 4/2011

OTHER PUBLICATIONS

Stumvoll M, Perriello G, Meyer C, Gerich J. 1999. Role of glutamine in human carbohydrate metabolism in kidney and other tissues. Kidney Int 55:778-792.*
Kidney Research UK Kidney Health Information sheet 2008.*
Welbourne et al., The Glutamine/Glutamate Couplet and Cellular Function, News Physiol. Sci., vol. 16, pp. 157-160, Aug. 2001.*
D'Agati et al., Focal Segmental Glomerulosclerosis, N. Engl J Med 2011;365:2398-2411.*
Hood et al., Protection of Acid-Base Balance by pH Regulation of Acid Production, NEJM, 339:12:819-826 (1998).*
Jones et al., Effect of pH on cardiorespiratory and metabolic response to exercise, J. Appl. Physiol.:Respirat. Eviron. Exercise Physiol. 43(6):959-964 (1977).*
Karinch et al., Glucocorticoids have a role in renal cortical expression of the SNAT3 glutamine transporter during chronic metabolic acidosis, Am J Physiol Renal Physiol 292: F448-F455 (2007).*
Schneider et al., Heterologous Expression of the Glutamine Transporter SNAT3 in Xenopus Oocytes Is Associated with Four Modes of Uncoupled Transport. The Journal of Biological Chemistry, Feb. 9, 2007, vol. 282, No. 6, pp. 3788-3798; Fig 1, 3-5, 8; p. 3793, col. 1, para 2, col. 2, para 1; p. 3796, col. 2, para 1.
Bongers, Clinical and Molecular Characterisation of Human Syndromes with Congenital Patellar Malformations. Manuscript, 1968; abstract; http://repository.ubn.ru.nl.
Patent Cooperation Treaty, "International Search Report and Written Opinion" by Authorized Officer Lee W. Young from ISA/US; dated Dec. 9, 2010.

* cited by examiner

*Primary Examiner* — Karlheinz R Skowronek
*Assistant Examiner* — Joseph Fischer
(74) *Attorney, Agent, or Firm* — Fish & Richardson P.C.

(57) ABSTRACT

Compositions are directed to the treatment of kidney diseases in a cell-specific manner. Methods of treating kidney diseases comprise the use of the compositions. Assays for identification of further compounds are provided. Biomarkers for predisposition to kidney diseases and diagnosis are indentified.

12 Claims, 13 Drawing Sheets

FIGURES 1A-1D
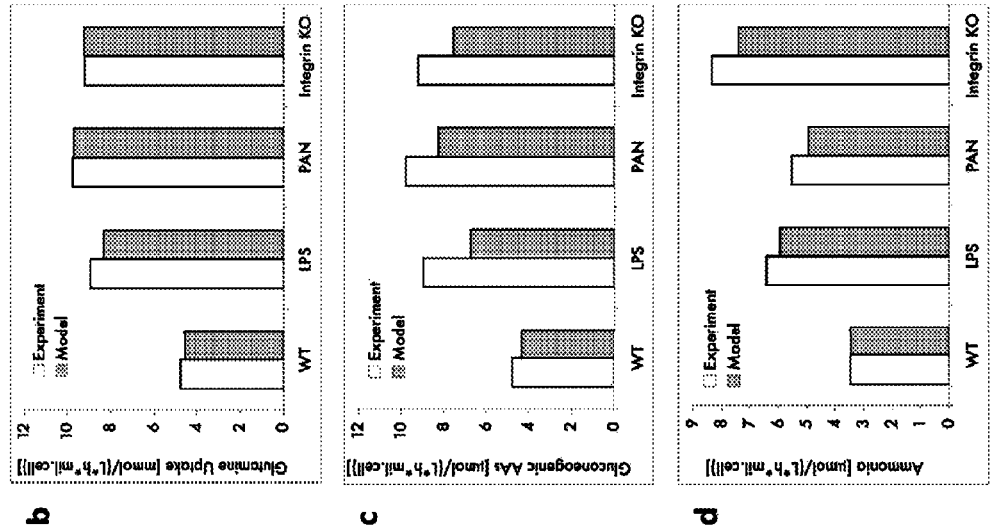
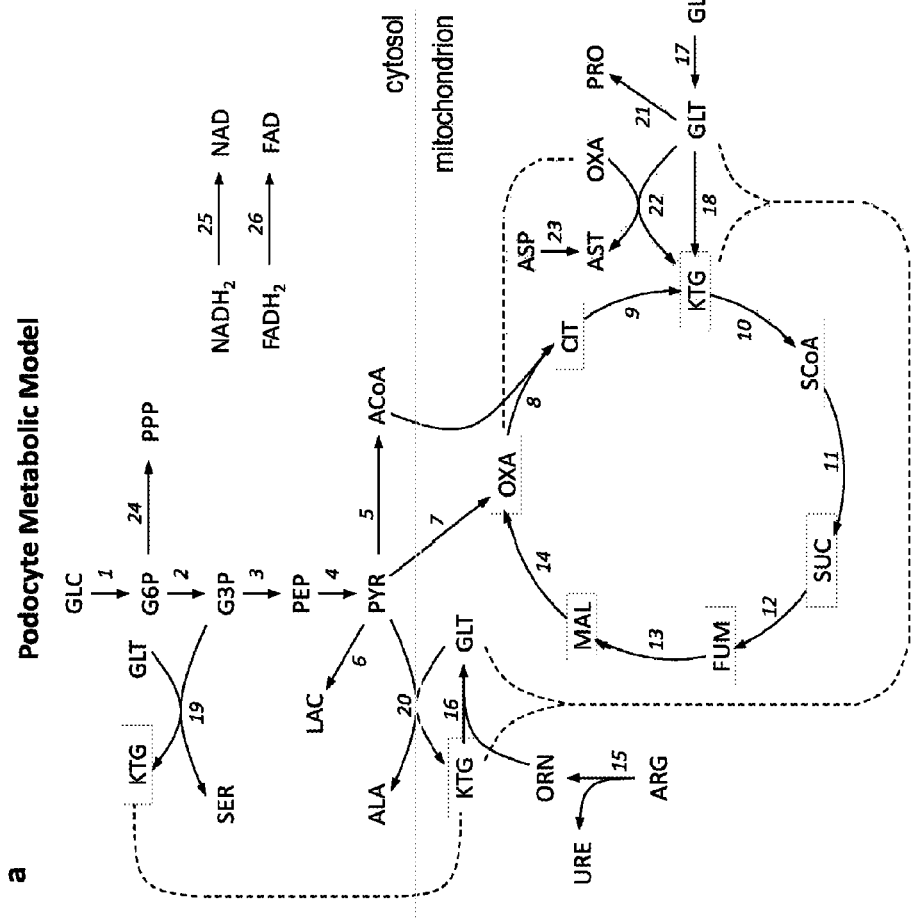

FIG. 10
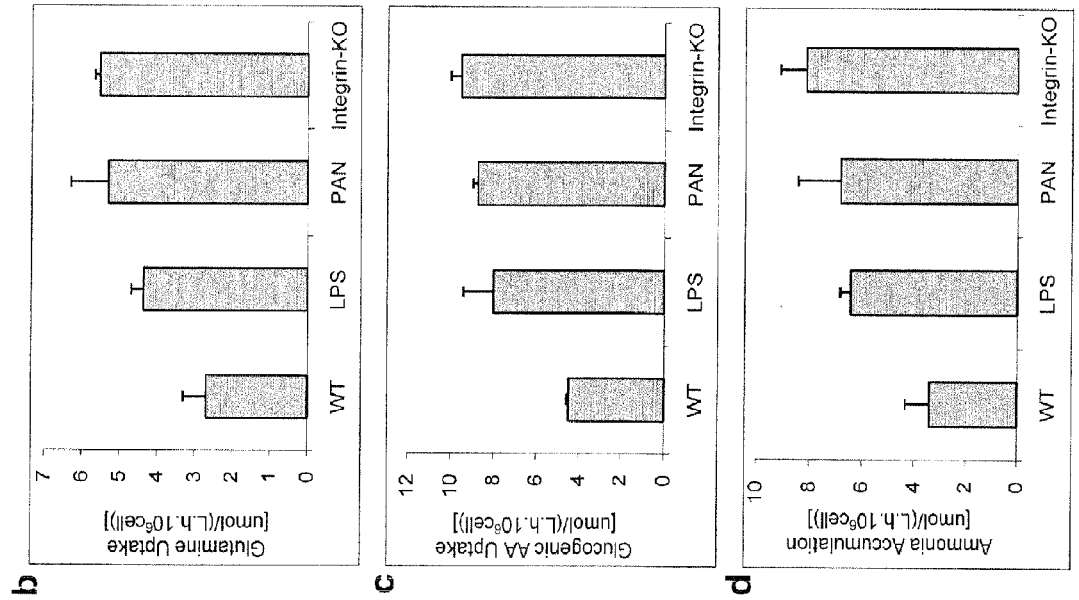
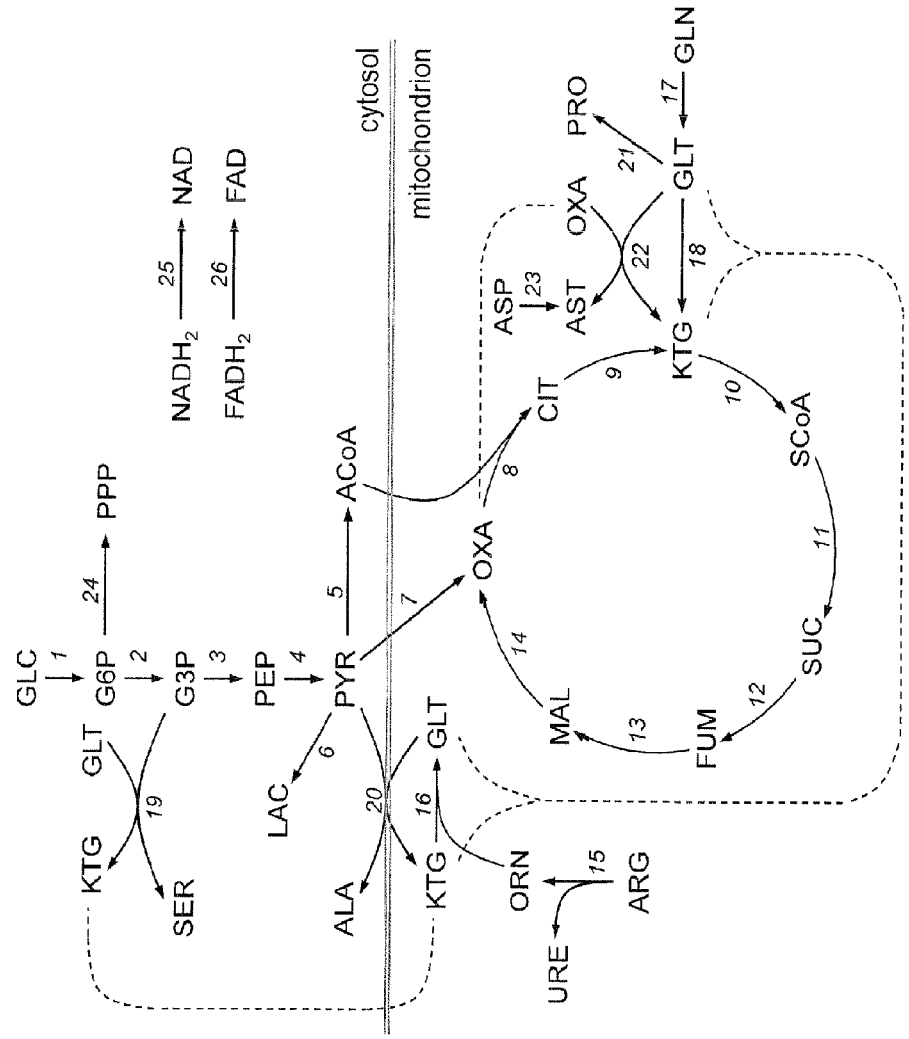

FIG. 13.
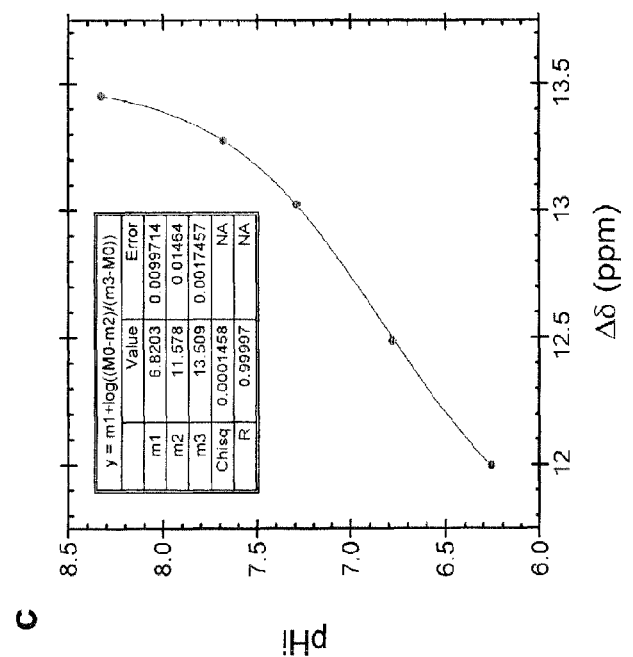
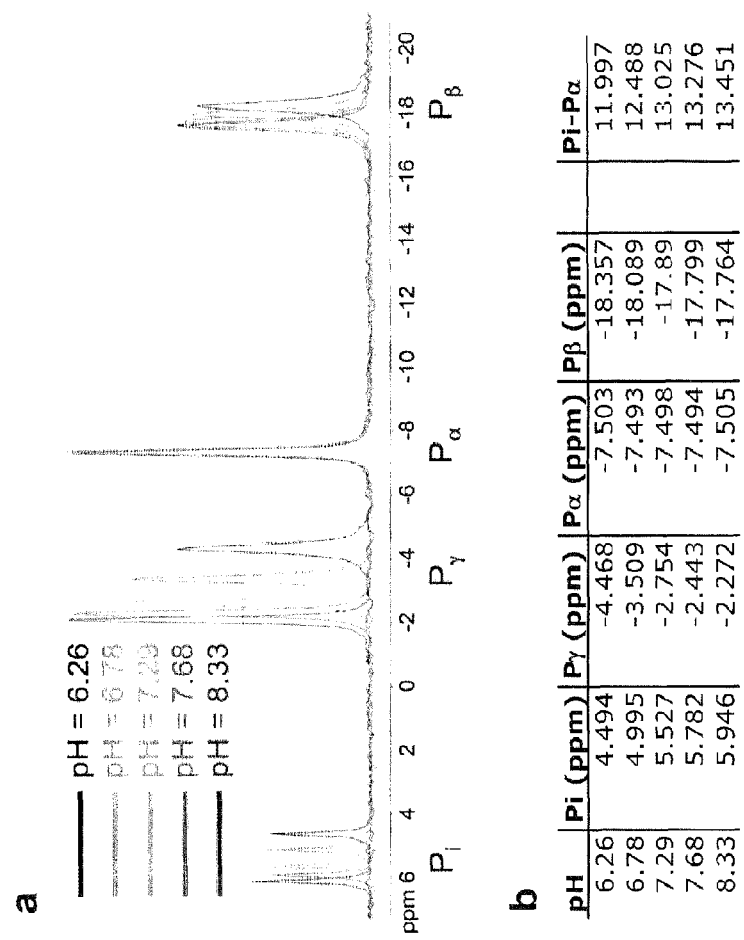

PODOCYTE PH MODULATION AND USES THEREOF

STATEMENT AS TO FEDERALLY FUNDED RESEARCH

This invention was made with United States government support under grant number R01 DK73495-01 awarded by the National Institutes of Health. The United States government has certain rights in the invention.

CROSS-REFERENCE TO RELATED APPLICATIONS

This application is a §371 national stage entry of International Application No. PCT/US2010/049777, filed Sep. 22, 2010, which claims the benefit of Provisional Application Ser. No. 61/244,604 filed Sep. 22, 2009, which is herein incorporated by reference in its entirety.

FIELD OF THE INVENTION

Embodiments of the invention comprise compositions which modulate the pH of podocytes, uses thereof and assays for the identification of further therapeutics.

BACKGROUND

Cathepsins are a family of enzymes that are part of the papain superfamily of cysteine proteases and include Cathepsins B, H, L, N and S. Cathepsins function in the normal physiological process of protein degradation in animals, including humans, e.g., in the degradation of connective tissue. However, elevated levels of these enzymes in the body can result in pathological conditions leading to disease. Thus, cathepsins have been implicated as causative agents in various disease states, including but not limited to, infections by *Pneumocystis carinii, Dypsanoma cruzi, Dypsanoma brucei brucei*, and *Crithidia fusiculata*; as well as in schistosomiasis, malaria, tumor metastasis, metachromatic leukodystrophy, muscular dystrophy, amytrophy, and the like.

SUMMARY

This Summary is provided to present a summary of the invention to briefly indicate the nature and substance of the invention. It is submitted with the understanding that it will not be used to interpret or limit the scope or meaning of the claims.

Proteinuria is serious sign of kidney impairment that is present in up to 500 million people around the world. Persistent proteinuria can lead to progression of kidney organ loss and is by itself a risk factor for cardiovascular morbidity and mortality. Heretofore, there has been no treatment available that targets the disease process of proteinuria or the progression in a cell-specific way. Identification of the cause of proteinuric disease, described herein, is a cathepsin L enzyme that is induced in the podocyte cytosol under disease conditions. The podocyte cytosol has a pH of around 7.0. At this pH, cytosolic, disease causing cathepsin L activity is active. The increase in cytosolic pH (alkalinization) to a pH around 7.5 blunts the activity of cathepsin L and stabilizes potential cleavage targets of the enzyme, thus protecting podocyte function and minimizing proteinuria.

Other aspects are described infra.

BRIEF DESCRIPTION OF THE DRAWINGS

FIG. 1A is a schematic of a podocyte metabolic model constructed based on available databases as well as mRNA and protein expression data extracted from podocytes. In FIGS. 1B-1D the following podocyte culture models were employed: wildtype (control), LPS and PAN stimulated podocytes (inducible injury models) as well as podocytes with genetic deletion of the alpha3 gene (genetic disease model). All injury cultures increase the uptake of glutamine as well as gluconeogenic amino acids. In addition, there is increasing ammonia production in diseased podocytes.

FIG. 10: (a) The metabolic network model for podocyte cultures. Arrows indicate the direction of reaction. (b, c) The uptake rates of glutamine and glucogenic amino acids for the control (WT) and disease (LPS, PAN, and α3 integrin-KO) models. (d) Ammonia production rate calculated by MFA.

Each bar represents the average from two separate experiments and the standard errors are shown as one-sided error bars (b-d).

Figure 11:
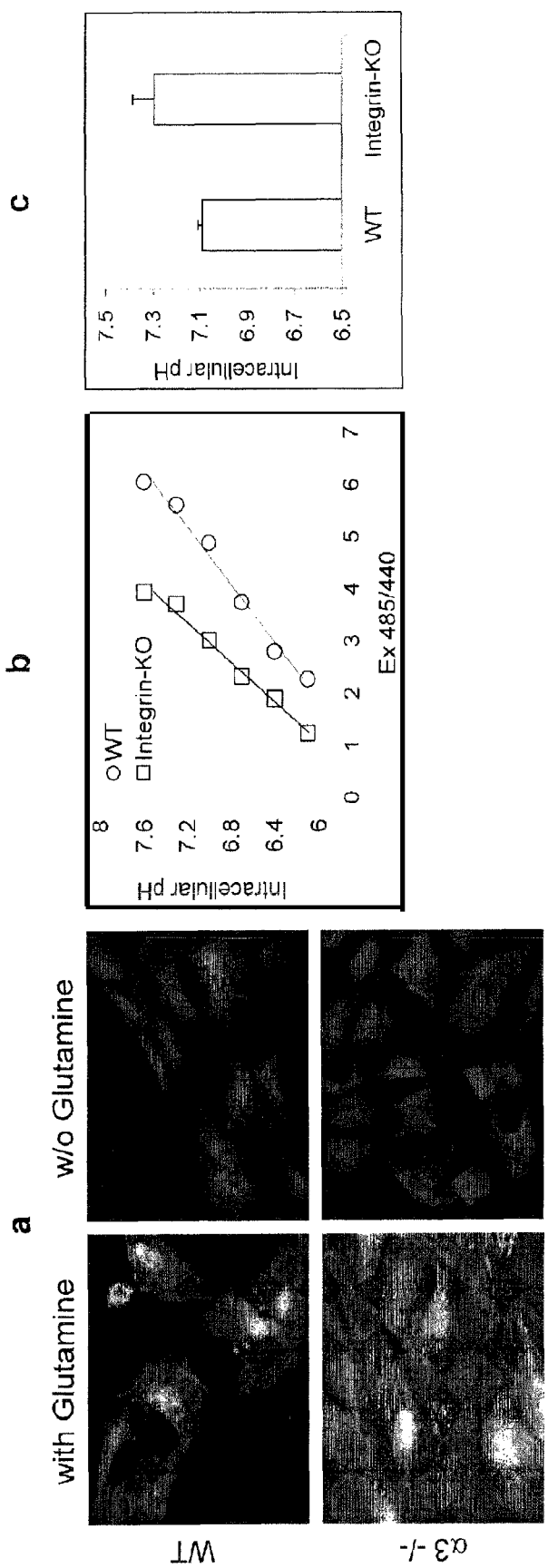

FIG. 11: The presence of glutamine in the medium affects the intracellular pH of cultured WT and a3 integrin deficient podocytes. WT podocytes grown in the presence of glutamine display a more alkaline pH in the cytoplasm and nuclei than cells grown in the absence of glutamine (a). A similar pattern is observed in a3 integrin deficient podocytes (a). Intracellular pH is monitored via the green fluorescent chloromethyl derivatives of fluorescein diacetate (CMFDA) that has good indicator function for pH ranges from 6.0 to 8.0 (b), (25). Increased fluorescence indicates a more alkaline environment (a, c), (25).

Figure 12:
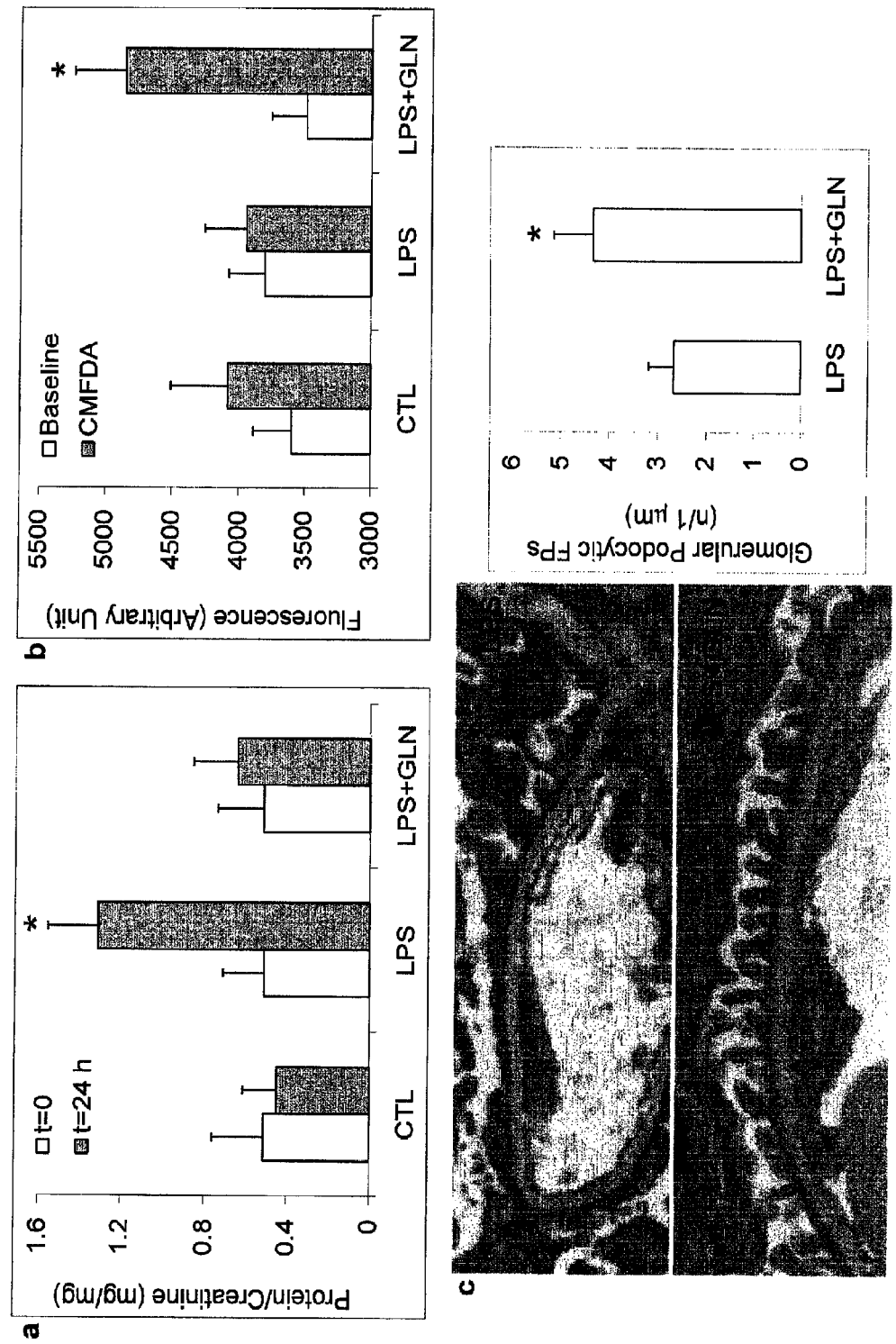

FIG. 12: Mice injected with PBS (CTL), LPS and LPS+Glutamine (GLN). Total volume of injections were 700 ml and total amount of glutamine and LPS injected for a 20 g mouse was 15 mg and 200 mg, respectively. (a) Proteinuria was assessed 24 h after injections. A statistically significant increase in proteinuria was observed in mice injected with LPS when compared to the values measured for mice injected with LPS+GLN after 24 h ($P<0.001$). Each data point represents at least 10 animals. (b) Glutamine injections are associated with increase in CMFDA fluorescence after LPS stimulation in mice, showing an increase in glomerular pH. Each data point represents at least 8 wells ($P<0.001$). (c) Representative electron microscopy images from the LPS (left, top) and LPS+Glutamine-injected mice (left, bottom) were used for morphometric analysis of podocyte FP effacement. The mean number of podocyte FPs along the GBM was evaluated within a distance of 1 mm (right). Each data point represents 10 different areas within the glomeruli ($P<0.01$).

FIG. 13: Intracellular pH calibration with ATP. RPMI 1640 medium was supplemented with 10 mM ATP and five solutions were prepared to span the full pH range (from 6.3 to 8.3). The spectra contained four major peaks: inorganic phosphate (resulting from $Na_2HPO_4$ in the medium), the g, a, and b peaks of ATP (a). The a peak of ATP was chosen as reference because it is the least likely phosphate variable to change with the pH (a and b). The spectral positions of major peaks were measured (B) and the calibration curve was generated (c) to quantitate intracellular pH with respect to the changes in the position of the inorganic phosphate ($P_i$-$P_a$).

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the present invention relates to discoveries involving agents which modulate the intra-podocyte pH and inhibit the enzymatic activity of cathepsin L. Embodiments include compositions which regulate the pH of podocytes, regulate cathepsin L activity, methods of use thereof and methods of delivery thereof. Embodiments further relate to the regulation of pathways by cathepsin L, by modulation of molecules on which cathepsin L interacts with directly or indirectly, e.g. CD2AP. Accordingly, the methods of the present invention can be used to treat disorders characterized by proteinuria.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "kidney disease(s)" and "kidney disorder(s)" are interchangeable and mean any disease, disorder, syndrome, anomaly, pathology, or abnormal condition of the kidney or of the structure or function of its constituent parts.

As used herein "proteinuria" refers to any amount of protein passing through a podocyte that has suffered podocyte damage or through a podocyte mediated barrier that normally would not allow for any protein passage. In an in vivo system the term "proteinuria" refers to the presence of excessive amounts of serum protein in the urine. Proteinuria is a characteristic symptom of either renal (kidney), urinary, pancreatic distress, nephrotic syndromes (i.e., proteinuria larger than 3.5 grams per day), eclampsia, toxic lesions of kidneys, and it is frequently a symptom of diabetes mellitus. With severe proteinuria general hypoproteinemia can develop and it results in diminished oncotic pressure (ascites, edema, hydrothorax).

As used herein "a patient in need thereof" refers to any patient that is affected with a disorder characterized by proteinuria. In one aspect of the invention "a patient in need thereof refers to any patient that may have, or is at risk of having a disorder characterized by proteinuria.

As used herein, the term "test substance" or "candidate therapeutic agent" or "agent" are used interchangeably herein, and the terms are meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. A test substance or agent can be assayed in accordance with the methods of the invention at any stage during clinical trials, during pre-trial testing, or following FDA-approval.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

As defined herein, a "therapeutically effective" amount of a compound (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

The term "sample" is meant to be interpreted in its broadest sense. A "sample" refers to a biological sample, such as, for example; one or more cells, tissues, or fluids (including, without limitation, plasma, serum, whole blood, cerebrospinal fluid, lymph, tears, urine, saliva, milk, pus, and tissue exudates and secretions) isolated from an individual or from cell culture constituents, as well as samples obtained from, for example, a laboratory procedure. A biological sample may comprise chromosomes isolated from cells (e.g., a spread of metaphase chromosomes), organelles or membranes isolated from cells, whole cells or tissues, nucleic acid such as genomic DNA in solution or bound to a solid support such as for Southern analysis, RNA in solution or bound to a solid support such as for Northern analysis, cDNA in solution or bound to a solid support, oligonucleotides in solution or bound to a solid support, polypeptides or peptides in solution or bound to a solid support, a tissue, a tissue print and the like.

Numerous well known tissue or fluid collection methods can be utilized to collect the biological sample from the subject in order to determine the level of DNA, RNA and/or polypeptide of the variant of interest in the subject. Examples include, but are not limited to, fine needle biopsy, needle biopsy, core needle biopsy and surgical biopsy (e.g., brain biopsy), and lavage. Regardless of the procedure employed, once a biopsy/sample is obtained the level of the variant can be determined and a diagnosis can thus be made.

Compositions

Proteinuria can be primarily caused by alterations of structural proteins involved in the cellular mechanism of filtration. The pathophysiological causes of proteinuria can be divided in the following major groups: (1) genetically determined disturbances of the structures which form the "glomerular filtration unit" like the glomerular basement membrane (GBM), the podocytes, or the slit diaphragm, (2) inflammatory processes, either directly caused by autoimmune processes or indirectly induced by microbes, (3) damage of the glomeruli caused by agents, or (4) as the final result of progressive tubulointerstitial injury finally resulting in the loss of function of the entire nephron.

The central metabolism of a cell can determine its short- and long-term structure and function. When a disease state arises, the metabolism (i.e., the transportation of nutrients into the cells, the overall substrate utilization and production, synthesis and accumulation of intracellular metabolites, etc.) is altered in a way that may permit the cell to adapt under the changing physiologic constraints. Diabetes mellitus is a metabolic disease that also affects podocytes, key cells that regulate glomerular filtration. A pathological role for a cytoplasmic variant of cathepsin L enzyme as the biological instigator of kidney filter dysfunction (proteinuria) and progression of renal disease through cleavage of different types of critical podocyte target proteins. Podocytes are highly differentiated cells that reside in the kidney glomeruli. Their foot processes (FP) and interposed slit diaphragm (SD) form the final barrier to protein loss. Podocyte injury is typically associated with FP effacement and urinary protein loss.

Without wishing to be bound by theory, this mechanism may be widely operative and also present in mediating the deleterious effects on the podocyte cytoskeleton during diabetic nephropathy. Cytoplasmic cathepsin L activity varies with the pH in the microenvironment and NMR-spectra analysis of the podocyte cytoplasm characterized the intrapodocyte pH close to 7.0. This offers an enormous possibility for alkalinization of the podocyte pH leading to a downshift of the enzymatic cathepsin L activity and thus provide renoprotection. One of the possibilities to alkalinize the podocyte cytosol is through the application of glutamine as shown in the examples section which follows.

Phosphorylation of synaptopodin by PKA or CaMKII promotes 14-3-3 binding, which protects synaptopodin against CatL-mediated cleavage, thereby stabilizing synaptopodin steady-state levels. Synaptopodin suppresses IRSp53:Mena-mediated filopodia by blocking the binding of Cdc42 and Mena to IRSp53 and induces stress fibers by competitive blocking the Smurf-1-mediated ubiquitination of RhoA. Synaptopodin also prevents the CatL-mediated degradation of dynamin. Synaptopodin stabilizes the kidney filter by blocking the re-organization of the podocyte actin cytoskeleton into a migratory phenotype. Dephosphorylation of synaptopodin by calcineurin abrogates the interaction with 14-3-3. This renders the CatL cleavage sites of synaptopodin accessible and promotes the degradation of synaptopodin. LPS or various other proximal signals induce the expression of B7-1 and CatL in podocytes, which cause proteinuria through the increased degradation of synaptopodin and dynamin. In parallel, LPS or other proximal signals can also activate Cdc42 and Rac1 though uPAR:β3 integrin signaling, through the loss of synaptopodin-mediated inhibition of Cdc42 signaling or through Nef:Src-mediated activation of Rac1. As a consequence, the podocyte actin cytoskeleton shifts from a stationary to a motile phenotype, thereby causing foot process effacement and proteinuria. CsA and E64 safeguard against proteinuria by stabilizing synaptopodin and dynamin steady-state protein levels in podocytes, FP(4)-Mito by blocking Cdcd42:IRSp53:Mena signaling, cycloRGDfV by blocking uPAR:β3 integrin signaling, NSC23766 by blocking Rac1 and Epleronone by blocking aldosterone signaling.

The enzymatic regulation of CD2AP in podocytes was characterized herein, and cathepsin L mediated remodeling of CD2AP as responsible event for the progression of renal disease towards end-stage renal failure were identified. CD2AP is a scaffolding protein containing three N-terminal SH3 domains. In the kidney, it is strongly expressed in glomerular podocytes, cells that regulate renal filtration. Homozygous CD2AP mutation or haplo-insufficiency of the human CD2AP gene confers susceptibility to glomerular disease and mice lacking CD2AP develop progressive kidney failure. The structural organization of CD2AP at 21 Å resolution reveals a tetrameric structure that exposes two cathepsin L cleavage sites. CD2AP is processed into a 32 kD C-terminal, structurally competent core protein that lacks SH3 domains and permits the release of the slit diaphragm protein dendrin, that in turn translocates to the podocyte nucleus to promote podocyte apoptosis. Enzymatic remodeling of CD2AP by cytosolic cathepsin L occurs in human and murine progressive kidney disease. Cathepsin L knockout mice with serum nephritis and wild type mice expressing cleaving resistant CD2AP are protected from nuclear dendrin and glomerular disease progression. The data herein show that the proteolytic regulation of CD2AP constitutes a critical factor for renal disease progression.

Further, in the examples section which follows, the data show that regulation of podocyte pH inhibits cathepsin L enzymatic activity whereby cathepsin L was shown to be the main cause of proteinuric disease. Thus, in a preferred embodiment, a composition regulates podocyte pH and inhibits expression and/or activity of cathepsin L. The agent can be any agent that modulates the pH of podocytes, for example, glutamine, or can be an agent that directly modulates expression of cathepsin L or the activity of cathepsin L, such as for example, antisense oligonucleotides, antibodies, small molecules, and the like. Combinations of agents which cause a rise in pH values in the podocytes to an alkaline pH environment and a cathepsin-L inhibitor can be used. In addition, combinations of alkalinizing agents which modulate intra-podocyte pH values can be used in therapy. (See, below).

The efficacy of the agents in preventing, treating or reversing kidney disease, such as for example, proteinuria, progressive renal disease, kidney transplantation, can be monitored through various diagnostics such as measurements of urinary protein concentrations.

The pH of a podocyte can be measured in various ways. See, for example, FIG. 3A. Podocyte pH was assessed with CMFDA—an indicator for pH. Higher green signal is consistent with a more alkaline cell.

Another example is using phosphorus NMR spectra for untreated and LPS-treated podocytes. Briefly, podocytes are cultured and treated with LPS. $8 \times 10^7$ to $1 \times 10^8$ cells are harvested and cultured in phosphate-free medium prior to assay. Phosphorous NMR spectra are acquired and analyzed using an iNMR software package. Intracellular pH (pHi) is calculated from the chemical shift difference (d) between the intracellular inorganic phosphate peak (Pi) and the primary phosphate of nucleoside phosphates (Pa) using equation 1.

$$pH_i = 6.82 + \log\left(\frac{d - 11.58}{13.51 - d}\right) \qquad \text{Eq. 1}$$

A reference sample containing 2.2 mM disodium phosphate and 10 mM ATP can be used to calibrate the pHi equation. The pH is varied from 6-8 and the dependence of the chemical shift difference (d) between the inorganic phosphate peak and the alpha-phosphate peak of ATP (Pα) is fit to obtain the constants of equation 1.

In a preferred embodiment the agent increases the pH of podocytes by about 5% as compared to a normal control, preferably by about 10%, preferably by about 50%, preferably by about 80%, 90%, 100%.

In a preferred embodiment, the intra-podocyte pH is increased to at least about 7.5. The podocyte cytosol has a pH of about 7.0. At this pH, cytosolic, disease causing cathepsin L activity is active. It was found (see, the examples section which follows) that an increase in pH to about 7.5 blunts the activity of cathepsin L and stabilizes potential cleavage targets of the enzyme, thus protecting podocyte function and treating proteinuria.

In another preferred embodiment, agents which modulate the podocyte pH and/or cathepsin-L activity or expression comprise oligonucleotides, polynucleotides, peptides, polypeptides, antibodies, aptamers, small molecules, organic molecules, inorganic molecules or combinations thereof.

In another preferred embodiment, the composition comprises one or more agents which modulate the intra-podocyte pH, modulate cathepsin L activity or modulate intra-podocyte pH and modulate cathepsin L activity. For example, one agent directly alters the pH of the podocyte and inhibits cathepsin L activity. In another example, an agent directly alters the pH of the podocyte and inhibits cathepsin L activity and a second agent directly targets cathepsin L, by, for example, binding to it such as an antibody, an antisense oligonucleotide which inhibits cathepsin L expression, an agent which targets another molecule in the cathepsin L synthesis pathway, or molecules in pathways which are targeted by cathepsin L, such as for example, dynamin, CD2AP, synaptopodin, etc. In another example, a composition comprises two agents whereby both modulate the pH of the podocytes.

In a preferred embodiment, the invention includes a method for reducing proteinuria or urinary albumin in a subject. In this method, the subject is administered a sufficient amount of an agent that modulates intra-podocyte pH values and/or cathepsin L expression, function, such that proteinuria or concentrations of urinary albumin are reduced by at least 10, 20, 30, 40, 50, 60, 70, 80, 90 or more percent post-treatment.

In another preferred embodiment, a method of treating a disease or disorder associated with pathological cathepsin L expression and/or activity comprises administering to a patient in need thereof, an effective amount of an agent which modulates intra-podocyte pH in vivo for treating the disorders. Preferably, the agent increases the intra-podocyte pH in vivo as compared to a control, such as, for example, glutamine. Glomerular disease is an enzymatic disease. Glutamine blunts the damaging activity of induced cytosolic CatL during podocyte injury by modulating intracellular pH.

Therefore, the optimization of glutamine metabolism fluxes and/or the intracellular pH would lead to novel therapeutic approaches.

In another preferred embodiment, a combination of agents which modulate infra-podocyte pH are administered to a patient.

In another preferred embodiment, a method of treating a disease or disorder characterized or associated with proteinuria comprises administering to a patient, comprising administering to a patient in need thereof, an effective amount of an agent which modulates intra-podocyte pH in vivo for treating the disease or disorder characterized by proteinuria. Preferably, the agent increases the intra-podocyte pH and inhibits expression and/or activity of cathepsin L.

In another preferred embodiment, a disease or disorder characterized by proteinuria comprising: glomerular diseases, membranous glomerulonephritis, focal segmental glomerulonephritis, minimal change disease, nephrotic syndromes, pre-eclampsia, eclampsia, kidney lesions, collagen vascular diseases, stress, strenuous exercise, benign orthostatic (postural) proteinuria, focal segmental glomerulosclerosis (FSGS), IgA nephropathy, IgM nephropathy, membranoproliferative glomerulonephritis, membranous nephropathy, sarcoidosis, Alport's syndrome, diabetes mellitus, kidney damage due to drugs, Fabry's disease, infections, aminoaciduria, Fanconi syndrome, hypertensive nephrosclerosis, interstitial nephritis, Sickle cell disease, hemoglobinuria, multiple myeloma, myoglobinuria, cancer, Wegener's Granulomatosis or Glycogen Storage Disease Type 1.

Podocyte diseases or disorders include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In another aspect, the diminution of podocyte density could be due to a decrease in a podocyte number, for example, due to apoptosis, detachment, lack of proliferation, DNA damage or hypertrophy.

In one embodiment, the podocyte-related (characterized) disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgesic or anticancer agent), an organ failure, an organ transplantation, or uropathy. In one aspect, ischemia can be sickle-cell anemia, thrombosis, transplantation, obstruction, shock or blood loss. In one aspect, the genetic disorders may include congenital nephritic syndrome of the Finnish type, the fetal membranous nephropathy or mutations in podocyte-specific proteins, such as α-actin-4, podocin and TRPC6.

In another preferred embodiment, a podocyte-related disease or disorder can be an abnormal expression or function of slit diaphragm proteins such as podocin, nephrin, CD2AP, cell membrane proteins such as TRPC6, and proteins involved in organization of the cytoskeleton such as synaptopodin, actin binding proteins, lamb-families and collagens. In another aspect, the podocyte-related disease or disorder can be related to a disturbance of the glomerular basement membrane (GBM), to a disturbance of the mesangial cell function, and to deposition of antigen-antibody complexes and anti-podocyte antibodies. In another aspect, the podocyte-related disease or disorder can be tubular atrophy.

In a preferred embodiment, the podocyte-related disease or disorder comprises proteinuria, such as microalbumiuria or macroalbumiuria.

In one aspect, the podocyte-related disease or disorder can be due to an abnormal expression or function of nephrin, podocin, FAT-1, CD2AP, Neph1, integrins, integrin-linked kinase, secreted protein acid rich in cysteine, Rho GTPases, α-actinin-4, synaptopodin, cyclin-dependent kinase5, podocalyxin, hic-5, GLEPP, TRPC6, dendrin, desmin, snail, notch, synaptopodin, HSP27, lamb4, podocalyxin, NHERF2, Ezrin, α,β-dystroglycans, α3 β1 integrin collagen type 4 or Wnt-4.

In another preferred embodiment, a method of treating podocyte injury or damage comprises administering to a subject an agent which increases the intra-podocyte pH values to at least a pH of 7.0. Podocytes can be injured in a variety of diseases, resulting in the glomerular filtration barrier damage. The fate of the podocyte then depends on factors such as the persistence of the initial injury and/or reparative mechanisms. If the initial injury is halted and the reparative mechanisms are present, there may be resolution. However, if the early structural changes in podocytes are not reversed, severe and progressive damage develops. This involves podocyte vacuolization, pseudocyst formation, and detachment of podocytes from the GMB, resulting in podocyte depletion. These events if unchanged may lead to the formation of synechiae via attachment of parietal epithelial cells of Bowman's capsule to denuded GBM areas.

Another consequence of injury or damage to podocyte is a decrease in podocyte number, or podocytopenia. The etiology of podocytopenia includes apoptosis, detachment, and the inability or lack of podocytes to proliferate. Total podocyte number is a balance between proliferation and loss. Podocyte number can be reduced by either a decrease in proliferation due to lack of DNA synthesis, DNA damage or hypertrophy, and/or an increase in podocyte loss due to detachment and apoptosis.

Acquired podocyte diseases can be immune and non-immune mediated. Examples of immune-mediated forms of podocyte injury include membranous nephropathy, minimal change disease and membranoproliferative glomerulonephritis associated with cryoglobulins. Non-immune causes of acquired podocyte injury include infectious causes such as HIV-associated nephropathy due to the local infection of podocytes by the HIV virus. It has been speculated that Parvo B19 virus may induce collapsing glomerulopathy in HIV-negative patients. Other examples of metabolic causes include diabetes, the metabolic syndrome and systemic hypertension, any cause of a reduced nephron number such as reflux nephropathy or chronic glomerulopathies, as well as infiltrative diseases of podocytes such as amyloid, where individual amyloid spicules "project" through the GBM, penetrating into the overlying podocytes.

In a preferred embodiment, these podocyte-related diseases or disorders are treated or prevented in individuals at risk of developing podocyte-related diseases or disorders by administration of one or more agents or compositions thereof which modulate pH of podocytes and/or inhibit expression or activity of cathepsin L. These agents can also be combined with one or more other chemotherapeutic compounds which are used to treat any of the diseases or disorders associated with proteinuria or podocyte injury.

A wide variety of agents can be used to target cathepsins, especially cathepsin L. These agents may be designed to target cathepsins by having an in vivo activity which reduces the expression and/or activity of cathepsin L.

The agents may target fat regulating cathepsin L based on the cDNA or regulatory regions of cathepsin L. For example, DNA-based agents, such as antisense inhibitors and ribozymes, can be utilized to target both the introns and exons of the cathepsin genes as well as at the RNA level.

Alternatively, the agents may target cathepsin L based on the amino acid sequences including the propieces and/or three-dimensional protein structures of cathepsin L. Protein-based agents, such as human antibody, non-human monoclonal antibody and humanized antibody, can be used to specifically target different epitopes on cathepsin L. Peptides or peptidomimetics can serve as high affinity inhibitors to specifically bind to the active site of a particular cathepsin, thereby inhibiting the in vivo activity of the cathepsin. Small molecules may also be employed to target cathepsin, especially those having high selectivity toward cathepsin L.

In addition to targeting cathepsin L, agents may also be used which competitively inhibit cathepsin L by competing with the natural substrates of cathepsins for binding with the enzymes.

In another embodiment, one of the agents can be a are protease inhibitor, specific for cathepsin L. Inhibitors of cathepsins include cathepsin L, B, and D inhibitors, antisense to cathepsin, siRNA, and antisense-peptide sequences. Examples of cathepsin inhibitors include but are not limited to epoxysuccinyl peptide derivatives [E-64, E-64a, E-64b, E-64c, E-64d, CA-074, CA-074 Me, CA-030, CA-028, etc.], peptidyl aldehyde derivatives [leupeptin, antipain, chymostatin, Ac-LVK-CHO$_5$ Z-Phe-Tyr-CHO, Z-Phe-Tyr(OtBu)-CO-CHO.H$_2$O, 1-Naphthalenesulfonyl-Ile-Trp-CHO, Z-Phe-Leu-COCHO.H$_2$O, etc.], peptidyl semicarbazone derivatives, peptidyl methylketone derivatives, peptidyl trifluoromethylketone derivatives [Biotin-Phe-Ala-fluoromethyl ketone, Z-Leu-Leu-Leu-fluoromethyl ketone minimum, Z-Phe-Phe-fluoromethyl ketone, N-Methoxysuccinyl-Phe-HOMO-Phe-fluoromethyl ketone, Z-Leu-Leu-Tyr-fluoromethyl ketone, Leupeptin trifluoroacetate, ketone, etc.], peptidyl halomethylketone derivatives [TLCK, etc.], bis(acylamino)ketone [1,3-Bis(CBZ-Leu-NH)-2-propanone, etc.], peptidyl diazomethanes [Z-Phe-Ala-CHN$_2$, Z-Phe-Thr (OBzl)-CHN$_2$, Z-Phe-Tyr (O-t-But)-CHN$_2$, Z-Leu-Leu-Tyr-CHN$_2$, etc.], peptidyl acyloxymethyl ketones, peptidyl methylsulfonium salts, peptidyl vinyl sulfones [LHVS, etc.], peptidyl nitriles, disulfides [5,5'-dithiobis[2-nitrobenzoic acid], cysteamines, 2,2'-dipyridyl disulfide, etc.], non-covalent inhibitors [N-(4-Biphenylacetyl)-S-methylcysteine-(D)-Arg-Phe-b-phenethylamide, etc.], thiol alkylating agents [maleimides, etc], azapeptides, azobenzenes, O-acylhydroxamates [Z-Phe-Gly-NHO-Bz, Z-FG-NHO-BzOME, etc.], lysosomotropic agents [chloroquine, ammonium chloride, etc.], and inhibitors based on Cystatins [Cystatins A, B, C, stefins, kininogens, Procathepsin B Fragment 26-50, Procathepsin B Fragment 36-50, etc.].

In another embodiment, the invention provides methods for inhibiting at least one enzymatic activity of cathepsin L. In one embodiment the cathepsin L inhibitors comprise: Z-Phe-Phe-FMK, H-Arg-Lys-Leu-Trp-NH$_2$, N-(1-Naphthalenyl-sulfonyl)-ile-Trp-aldehyde, Z-Phe-Tyr(tBu)-diazomethylketone, or Z-Phe-Tyr-aldehyde.

Nucleic Acid-Based Agents:

Nucleic acid-based agents such as antisense molecules and ribozymes can be utilized to target both the introns and exons of the cathepsin genes as well as at the RNA level to inhibit gene expression thereof, thereby inhibiting the activity of the targeted cathepsin. Further, triple helix molecules may also be utilized in inhibiting the cathepsin gene activity. Such molecules may be designed to reduce or inhibit either the wild type cathepsin gene, or if appropriate, the mutant cathepsin gene activity. Techniques for the production and use of such molecules are well known to those of skill in the art, and are succinctly described below.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. Wagner (1994) *Nature* 372:333-335. For example, oligonucleotides complementary to either the 5'- or 3'-untranslated, non-coding regions of the human or mouse gene of cathepsin L could be used in an antisense approach to inhibit translation of endogenous cathepsin L mRNA.

Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target gene mRNA, antisense nucleic acids are preferably at least six nucleotides in length, and are more preferably oligonucleotides ranging from 6 to about 50 nucleotides in length. In specific aspects the oligonucleotide is at least 10 nucleotides, preferably at least 17 nucleotides, more preferably at least 25 nucleotides and most preferably at least 50 nucleotides.

Alternatively, antisense molecules may be designed to target the translated region, i.e., the cDNA of the cathepsin gene. For example, the antisense RNA molecules targeting the full coding sequence or a portion of the mature murine cathepsin L (Kirschke et al. (2000) *Euro. J. Cancer* 36:787-795) may be utilized to inhibit expression of cathepsin L and thus reduce the activity of its enzymatic activity. In addition, a full length or partial cathepsin L cDNA can be subcloned into a pcDNA-3 expression vector in reversed orientation and such a construct can be transfected into cells to produce antisense polyRNA to block endogenous transcripts of a cathepsin, such as cathepsin L, and thus inhibit the cathepsin's expression.

In vitro studies may be performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides, or agents facilitating transport across the cell membrane (See, e.g., Letsinger (1989) *Proc. Natl. Acad. Sci. U.S.A.* 86:6553-6556) or the blood-brain barrier, hybridization-triggered cleavage agents. See, e.g., Krol (1988) *Bio Techniques* 6:958-976 or intercalating agents. See, e.g., Zon (1988) *Pharm. Res.* 5:539-549. The oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group consisting of, but not being limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil,2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine.

The antisense oligonucleotide may also comprise at least one modified sugar moiety selected from the group consisting of, but not being limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Ribozyme molecules designed to catalytically cleave target gene mRNA transcripts can also be used to prevent translation of target gene mRNA and, therefore, expression of target gene product. See, e.g. Sarver et al. (1990) *Science* 247:1222-1225.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage event. The composition of ribozyme molecules should include one or more sequences complementary to the target gene mRNA, and should include the well known catalytic sequence responsible for mRNA cleavage.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art.

Endogenous cathepsin gene expression can also be reduced by inactivating or "knocking out" the targeted cathepsin gene or its promoter using targeted homologous recombination. Smithies et al. (1985) *Nature* 317:230-234; Thomas and Capecchi, (1987) *Cell* 51:503-512; and Thompson et al. (1989) *Cell* 5:313-321.

Alternatively, endogenous cathepsin gene expression can be reduced by targeting deoxyribonucleotide sequences complementary to the regulatory region of the cathepsin gene (i.e., the target gene promoter and/or enhancers) to form triple helical structures that prevent transcription of the target gene in target cells in the body. See generally, Helene (1991) *Anticancer Drug Des.* 6:569-584; Helene et al. (1992) *Ann. N.Y. Acad. Sci.* 660:27-36; and Maher (1992) *Bioassays* 14:807-815.

Nucleic acid molecules to be used in triplex helix formation for the inhibition of transcription should be single stranded and composed of deoxynucleotides. The base composition of these oligonucleotides must be designed to promote triple helix formation via Hoögsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Biomarkers

In a preferred embodiment, a biomarker for the diagnosis of a disease or disorder characterized by proteinuria and/or identification of individuals at risk of developing a disease or disorder characterized by proteinuria comprising: cathepsin-L, system N glutamine transporter (SNAT3), dynamin, synaptopodin or cytoskeletal regulator protein synaptopodin, cytoskeletal adaptor protein (CD2AP), variants, mutants or fragments thereof.

The biomarkers can be increased or decreased in expression relative to each other. The panel of biomarker expression profiles are compared to normal controls. In other instances, the intra-cellular localization changes with the progression of disease. For example, a fragment of CD2AP comprises p32 C-terminal fragment. As cathepsin-L cleaves the CD2AP, there is an increase in N-terminal CD2AP fragments and p32 fragments. The p32 cannot bind to dendrin, which is then trafficked to the podocyte nuclei. Thus, dendrin localization is altered during the disease progression.

In another preferred embodiment, the identification of an individual at risk of developing disease or disorder characterized by proteinuria detects at least one biomarker or fragments thereof.

In another preferred embodiment, the progression of disease or disorder characterized by proteinuria is correlated to an increase in cathepsin-L and/or system N glutamine transporter (SNAT3) expression and/or an increase in p32 CD2AP C-terminal fragment expression and/or dendrin in podocyte nuclei.

Candidate Therapeutic Agents:

In a preferred embodiment, methods (also referred to herein as "screening assays") are provided for identifying modulators, i.e., candidate or test compounds or agents (e.g., proteins, peptides, peptidomimetics, peptoids, small molecules, analogues or other drugs) which modulate the pH of podocytes and/or act directly on cathepsin L activity or expression or synthesis pathways thereof. Compounds thus identified can be used to modulate the activity of target gene products, prolong the half-life of a protein or peptide, regulate cell division, etc, in a therapeutic protocol, to elaborate the biological function of the target gene product, or to identify compounds that disrupt normal target gene interactions.

In another preferred embodiment, a high-throughput screening assay (HTS) screening assay is used to screen a diverse library of member compounds. The "compounds" or "candidate therapeutic agents" or "candidate agents" can be any organic, inorganic, small molecule, protein, antibody, aptamer, nucleic acid molecule, or synthetic compound.

In another preferred embodiment, the candidate agents modulate cathepsin enzymes, precursors or molecules involved in the pathways. Preferably, the enzyme is cathepsin L. These enzymes can be involved in various biochemical pathways such as synthetic pathways, breakdown pathways, e.g. ubiquitin, enzymatic pathways, protein trafficking pathways, metabolic pathways, signal transduction pathways, and the like.

In another preferred embodiment, the high throughput assays identifies candidate agents that target and modulate the pathways involved in the pathological expression or activity of cathepsin L. The candidate agents would be useful in developing and identifying novel agents for the treatment of diseases or disorders involved in proteinuria.

In one embodiment, the invention provides assays for screening candidate or test compounds which modulate the pH of podocytes. Agents which increase intra-podocyte pH values to at least pH 7.0 are preferred agents. An example of an agent is glutamine. Other amino acids which can be administered to patients comprise: alanine, arginine, asparagine, aspartic acid, cysteine, glutamic acid, glycine, histidine, isoleucine, leucine, lysine, methionine, phenylalanine, proline, serine, threonine, tryptophan, tyrosine, valine, analogs or variants thereof.

The agents can be used alone or in combinations with other therapeutic agents to treat patients.

In another embodiment, the invention provides assays for screening candidate or test compounds that bind to or modulate an activity of cathepsin L protein or polypeptide or a biologically active portion thereof; mutants or fragments, or fusion proteins thereof.

Candidate agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Other examples of candidate agents comprise: amino acids, nucleic acids, oligonucleotides, polynucleotides, peptide nucleic acids, peptides, polypeptides, antibodies, small molecules, organic or inorganic molecules, synthetic molecules, natural molecules, variants, analogs, or combinations thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the one-bead one-compound library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Nat'l Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In another preferred embodiment, the candidate therapeutic agent comprises proteins, peptides, organic molecules, inorganic molecules, nucleic acid molecules, and the like. These molecules can be natural, e.g. from plants, fungus, bacteria etc., or can be synthesized or synthetic.

A prototype compound may be believed to have therapeutic activity on the basis of any information available to the artisan. For example, a prototype compound may be believed to have therapeutic activity on the basis of information contained in the Physician's Desk Reference. In addition, by way of non-limiting example, a compound may be believed to have therapeutic activity on the basis of experience of a clinician, structure of the compound, structural activity relationship data, $EC_{50}$ assay data, $IC_{50}$ assay data, animal or clinical studies, or any other basis, or combination of such bases.

A therapeutically-active compound is a compound that has therapeutic activity, including for example, the ability of a compound to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against any disease or disorder associated with proteinuria. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

Candidate compounds for use with an assay of the present invention or identified by assays of the present invention as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

Candidate compounds can be isolated, from microorganisms, animals or plants, for example, and can be produced recombinantly, or synthesized by chemical methods known in the art. If desired, candidate compounds of the present invention can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries. The other four approaches are applicable to polypeptide, non-peptide oligomer, or small molecule libraries of compounds and are preferred approaches in the present invention. See Lam, *Anticancer Drug Des.* 12: 145-167 (1997).

In an embodiment, the present invention provides a method of identifying a candidate compound as a suitable prodrug. A suitable prodrug includes any prodrug that may be identified by the methods of the present invention. Any method apparent to the artisan may be used to identify a candidate compound as a suitable prodrug.

In another aspect, the present invention provides methods of screening candidate compounds for suitability as therapeutic agents. Screening for suitability of therapeutic agents may include assessment of one, some or many criteria relating to the compound that may affect the ability of the compound as a therapeutic agent. Factors such as, for example, efficacy, safety, efficiency, retention, localization, tissue selectivity, degradation, or intracellular persistence may be considered. In an embodiment, a method of screening candidate compounds for suitability as therapeutic agents is provided, where the method comprises providing a candidate compound identified as a suitable prodrug, determining the therapeutic activity of the candidate compound, and determining the intracellular persistence of the candidate compound. Intracellular persistence can be measured by any technique apparent to the skilled artisan, such as for example by radioactive tracer, heavy isotope labeling, or LCMS.

In screening compounds for suitability as therapeutic agents, intracellular persistence of the candidate compound is evaluated. In a preferred embodiment, the agents are evaluated for their ability to modulate the intracellular pH may comprise, for example, evaluation of intracellular pH over a period of time in response to a candidate therapeutic agent. In a preferred embodiment, the intra-podocyte pH in the presence or absence of the candidate therapeutic compound in human tissue is determined. Any technique known to the art worker for determining intracellular pH may be used in the present invention. See, also, the experimental details in the examples section which follows.

A further aspect of the present invention relates to methods of inhibiting the activity of a condition or disease associated with proteinuria comprising the step of treating a sample or subject believed to have a disease or condition with a prodrug identified by a compound of the invention. Compositions of the invention act as identifiers for prodrugs that have therapeutic activity against a disease or condition. In a preferred aspect, compositions of the invention act as identifiers for drugs that show therapeutic activity against conditions including for example associated with proteinuria.

In one embodiment, a screening assay is a cell-based assay in which the activity of cathepsin L is measured against an increase or decrease of pH values in the cells. Determining the ability of the test compound to modulate the pH and determining cathepsin L activity, by various methods, including for example, fluorescence, protein assays, blots and the like. The cell, for example, can be of mammalian origin, e.g., human.

In another preferred embodiment, the screening assay is a high-throughput screening assay. The ability of a compound to modulate pH and/or modulate cathepsin L expression and/or activity can be evaluated as described in detail in the Examples which follow.

In another preferred embodiment, soluble and/or membrane-bound forms of isolated proteins, mutants or biologically active portions thereof, can be used in the assays if desired. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON™ X-100, TRITON™ X-114, THESIT™, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays can also be used and involve preparing a reaction mixture which includes cathepsin L and the test compound under conditions and time periods to allow the measurement of the cathepsin L activity over time, a range of pH values and concentrations of test agents.

The enzymatic activity can be also be detected, e.g., using fluorescence energy transfer (FET) (see, for example, Lakowicz et al., U.S. Pat. No. 5,631,169; Stavrianopoulos, et al, U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorometric detection means well known in the art (e.g., using a fluorimeter).

In another embodiment, determining the ability of the enzyme to bind or "dock" to its binding site on a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target product or the test substance is anchored onto a solid phase. The target product/test compound complexes anchored on the solid phase can be detected at the end of the reaction. Preferably, the target product can be anchored onto a solid surface, and the test compound, (which is not anchored), can be labeled, either directly or indirectly, with detectable labels discussed herein.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries:

Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA.* 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and nonpeptide lead discovery using robotically synthesized soluble libraries, *Can J. Physiol Pharmacol.* 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA,* 90:6909-6913 (1993)); vinylogous polypeptides (Hagihara, et al., *J. Amer. Chem. Soc.* 114:6568 (1992)); nonpeptidal peptidomimetics with β-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261: 1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309-314 (1996) and PCT/US96/10287); carbohydrate libraries (see, e.g., Liang, et al., *Science,* 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569, 588); thiazolidinones and metathiazanones (U.S. Pat. No. 5,549,974); pyrrolidines (U.S. Pat. Nos. 5,525,735 and 5,519, 134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

Small Molecules:

Small molecule test compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio., 1:60 (1997). In addition, a number of small molecule libraries are commercially available.

The whole procedure can be fully automated. For example, sampling of sample materials may be accomplished with a plurality of steps, which include withdrawing a sample from a sample container and delivering at least a portion of the withdrawn sample to test platform. Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

In one embodiment, auto-sampling may be done using a microprocessor controlling an automated system (e.g., a robot arm). Preferably, the microprocessor is user-programmable to accommodate libraries of samples having varying arrangements of samples (e.g., square arrays with "n-rows" by "n-columns," rectangular arrays with "n-rows" by "m-columns," round arrays, triangular arrays with "r-" by "r-" by "r-" equilateral sides, triangular arrays with "r-base" by "s-" by "s-" isosceles sides, etc., where n, m, r, and s are integers).

Automated sampling of sample materials optionally may be effected with an auto-sampler having a heated injection probe (tip). An example of one such auto sampler is disclosed in U.S. Pat. No. 6,175,409 B1 (incorporated by reference).

According to the present invention, one or more systems, methods or both are used to identify a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Generally, the automated system includes a suitable protocol design and execution software that can be programmed with information such as synthesis, composition, location information or other information related to a library of materials positioned with respect to a substrate. The protocol design and execution software is typically in communication with robot control software for controlling a robot or other automated apparatus or system. The protocol design and execution software is also in communication with data acquisition hardware/software for collecting data from response measuring hardware. Once the data is collected in the database, analytical software may be used to analyze the data, and more specifically, to determine properties of the candidate drugs, or the data may be analyzed manually.

Data and Analysis:

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing genetic information over networks such as the Internet.

Administration of Compositions to Patients

The compositions or agents identified by the methods described herein may be administered to animals including human beings in any suitable formulation. For example, the compositions for modulating protein degradation may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

The compounds can be administered with one or more therapies. The chemotherapeutic agents may be administered under a metronomic regimen. As used herein, "metronomic" therapy refers to the administration of continuous low-doses of a therapeutic agent.

Dosage, toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a compound (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

Other Methods of Detection of Podocyte Abnormalities and Podocyte-Related Disorders and Diseases:

One or more methods can be used in the detection of podocyte abnormalities in conjunction with the methods embodied herein if the health care provider wishes. In one aspect, early podocyte abnormalities can be detected using, for example, microscopy as described below. In the absence of a kidney biopsy, early diagnosis of podocyte-related diseases or disorders can be done on the basis of elevated excretion of protein (or albumin) into the urine.

One of the methods of detection of early podocyte damage is electron microscopy. Electron microscopy provides information about the presence and subcellular location of immune complexes (which are seen as electron-dense deposits), the degree of injury to glomerular cells, and the consistency of the basement membrane. Electron microscopy also detects fibrils and provides information on the ultrastructure of the kidney, such as podocyte effacement and flattening, which cannot be readily detected by light microscopy. Typical podocyte abnormalities include vacuolization, microcysctic or pseudocystic changes, the presence of cytoplasmic inclusion bodies, and detachment from the GBM. Others useful methods include light microscopy (e.g., to evaluate the shape of podocytes) and fluorescence microscopy (to localize and quantify stained proteins, e.g. proteins of the actin cytoskeleton).

Light microscopy describes glomerular cellularity, i.e., whether the number of glomerular cells is normal or increased (hypercellularity). Often light microscopy can distinguish which cell type (resident glomerular cells or infiltrating cells such as neutrophils) is increased; whether the GBMs are thickened and whether the capillary loops are patent, collapsed, or filled with material such as hyaline; and the presence or absence of glomerulosclerosis. Although the glomerulus is the primary site of injury in glomerular disease, the tubules and the interstitium must be carefully inspected because the degree of tubulointerstitial fibrosis is the best predictor of the prognosis in renal disease. The presence of glomerular crescents can also be detected on light microscopy. Crescents are layers of cells (parietal epithelial cells, podocytes, lymphocytes, and macrophages) in the Bowman space, and their presence signifies severe disease.

Immunofluorescent immunostaining determines the presence or absence of any underlying immune processes. Staining is directed against specific antibodies (e.g., IgG, IgA, and anti-GBM) and individual complement components (e.g., C3, C4, and C5b-9). The pattern of the immune components is also diagnostic. A granular pattern is typical of antigen-antibody complexes, such as in membranous nephropathy, whereas a linear pattern occurs in anti-GBM disease. The location of antibody or complement (e.g., in the mesangium in IgA nephropathy) also provides clues to the diagnosis. Immunostaining can determine the presence of matrix proteins (silver stain), amyloid fibrils (Congo red), and viral inclusions.

Disturbances in cultured podocyte functions can be studied by the use of activation, adherence, migration and proliferation assays. One indication of an early podocyte damage can be a disruption in the PINCH-1-ILK-α-parvin complex, resulting in the reduced podocyte-matrix adhesion, foot process formation or increase in apoptosis of podocytes. Another indicator of an early damage could be a disruption of function of synaptopodin, a member of a class of proline-rich actin associated proteins that are expressed in podocyte foot processes. It has been indicated that synaptopodin is essential for the integrity of the podocyte actin cytoskeleton and for the regulation of podocyte cell migration. See Yang et al, *J Am Soc Nephrol*. (2005) 16(7): 1966-76; Asanuma, K. et al., *Nat Cell Biol*. (2006) 8(5): 485-91; Pavenstadt et al, *Physiol Rev*. (2003) 83(1): 253-307. On the mRNA and protein level, specific podocyte genes including markers of cellular stress, apoptosis and specific proteins involved in the podocyte damage, can be studied as described in Tandon et al., *Am J Physiol Renal Physiol*. 2006, 17; Durvasula R. V., *Am J Physiol Renal Physiol*. (2005) 289(3): F577-84. In blood and urine samples podocyte damage can also be assessed (see Hara et al., *J Am Soc Nephrol*. (2005) 16(2): 408-16; Vogelmann et al. (2003) *Am J Physiol Renal Physiol*. 285(1): F40-8, Pavenstadt et al., *Physiol Rev*. (2003) 83(1): 253-307).

Podocyte loss can be detected with a high degree of sensitivity by the abnormal presence in urine sediment of a gene selectively expressed in the podocyte so as to be podocyte-specific in the urinary tract. Examples of markers useful for detection of podocyte damage include nephrin, glepp1, and Indian hedgehog.

In a preferred embodiment, a biomarker for the prognosis or diagnosis of a disease or disorder characterized by proteinuria and/or identification of individuals at risk of developing a disease or disorder characterized by proteinuria comprising: cathepsin-L, system N glutamine transporter (SNAT3), dynamin, synaptopodin or cytoskeletal regulator protein synaptopodin, cytoskeletal adaptor protein (CD2AP), variants, mutants, homologs or fragments thereof.

In a preferred embodiment, a fragment of CD2AP comprises p32 C-terminal fragment.

In another preferred embodiment, expression of dendrin is increased in podocyte nuclei as compared to normal baseline controls.

In another preferred embodiment, the progression of disease or disorder characterized by proteinuria is correlated to an increase in cathepsin-L and/or system N glutamine transporter (SNAT3) expression as compared to normal baseline controls. Preferably, the increase in cathepsin-L and/or system N glutamine transporter (SNAT3) expression is correlated to urinary protein concentration.

In another preferred embodiment, the progression of disease or disorder characterized by proteinuria is correlated to an increase in p32 CD2AP C-terminal fragment expression and/or dendrin in podocyte nuclei.

In one aspect, detection of a particular gene can be done using a reverse transcriptase quantitative polymerase chain reaction (RT-PCR), microarrays, Western blots, proteomics and in-situ hybridization, immunhisto- and immunocytochemistry. The markers can be detected from a biological sample, such as for example, biopsy specimen, urine or blood analysis.

Formulations

While it is possible for a composition to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Podocyte pH Modulation

Methods:
Podocyte Metabolic Model:

A podocyte metabolic model was constructed based on available databases as well as mRNA and protein expression data extracted from podocytes. The following podocyte culture models were employed: wildtype (control), LPS and PAN stimulated podocytes (inducible injury models) as well as podocytes with genetic deletion of the alpha3 gene (genetic disease model). All injury cultures increase the uptake of glutamine as well as gluconeogenic aminoacids. In addition, there is increasing ammonia production in diseased podocytes. These changes were predicted by the podocyte metabolic model and confirmed by measuring directly amino acids and ammonia (FIGS. 1A-1D).

Cathepsin L Activity Assay.

Subcellular sites of cathepsin L and cathepsin B activity in glomerular extracts were visualized by a fluorogenic substrate, CV-(FR)$_2$, which emits light upon cleavage by cathepsin L or cathepsin B (Biomol). Cathepsin L inhibitor Z-FF-FMK (Calbiochem) which does not inhibit cathepsin B was used for specific inhibition of cathepsin L.

Results:

The sodium-coupled neutral amino acid transporters (SNAT) of the SLC38 gene family contain SNATs 1-6 and glutamine emerges as a favored substrate throughout the family, except for SNAT4. Without wishing to be bound by theory, it hypothesized that the induction of SNAT3 and increased uptake of glutamine during podocyte disease would have pH modulating effect in the cytoplasm and reduce the activity of cytosolic 'short CatL'.

In brief, total RNA from cultured mouse podocytes was isolated with RNA isolation kit (Qiagen, Germantown, Md.) and the amount of RNA was measured by spectrophotometry. Purified RNA was reverse transcribed and PCR performed using PCR Mastercycler (Eppendorf, Westbury, N.Y.).

Figures 2A, 2B:
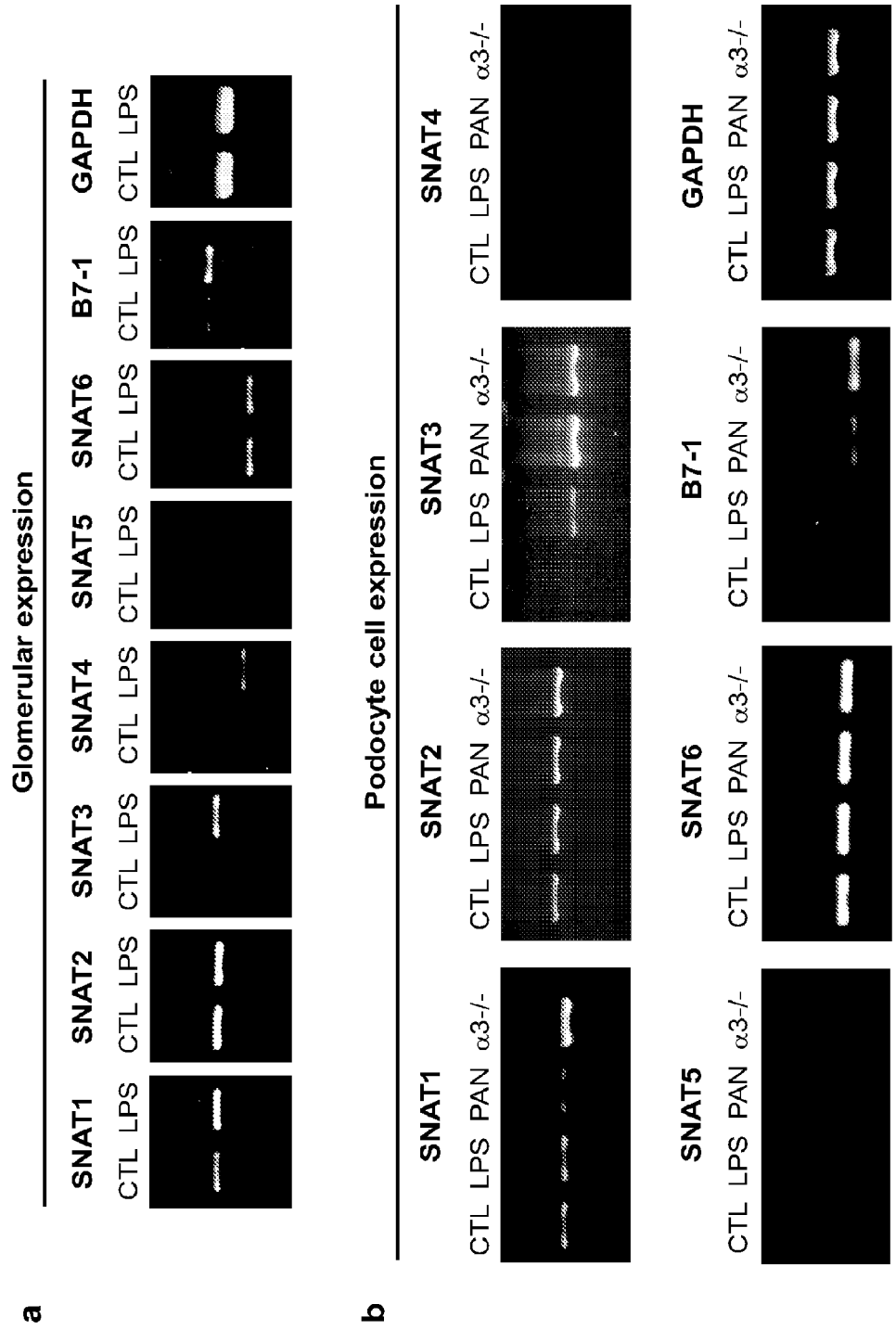
FIGS. 2A, 2B are scans of blots showing increased mRNA expression of glutamine transporters SNAT 1-6 in cultured mouse podocytes and mouse glomeruli.

The expression patterns of the SNAT family were analyzed in glomeruli and cultured podocytes. The results from experiments shown in FIGS. 2A, 2B show increased mRNA expression of glutamine transporters SNAT 1-6 in cultured mouse podocytes and mouse glomeruli.

Figure 3A:
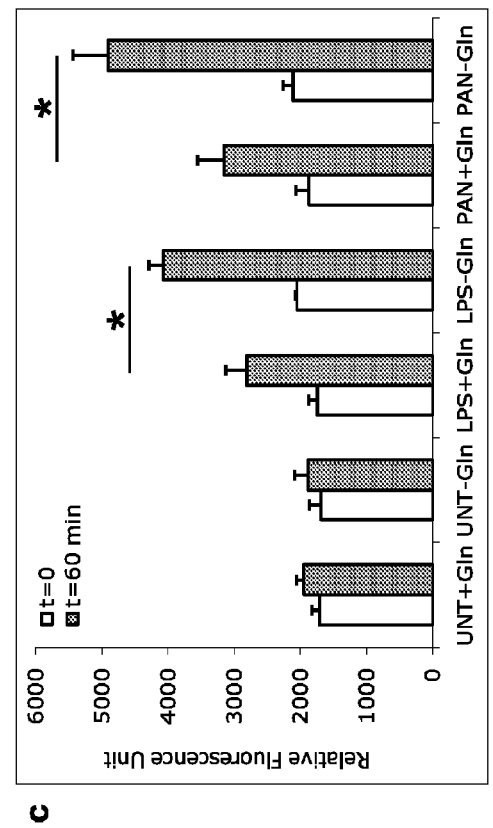
FIG. 3A is a scan of a photograph showing intracellular pH of podocytes with or without glutamine. Podocyte pH assessed with CMFDA—an indicator for pH. Higher green signal is consistent with a more alkaline cell. The presence of high glutamine levels in cell culture media alkalinizes the normal podocytes as well as podocytes that lack integrin alpha3 beta1 (genetic model cells for podocyte disease).
Figure 3B:
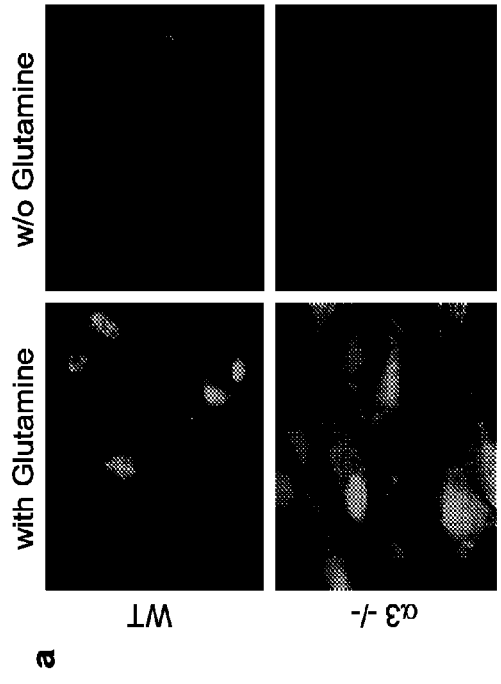
FIGS. 3B, 3C are graphs showing that both LPS and PAN treatment stimulate cathepsin L activity in podocytes. Cathepsin L activity is lower in the presence of high glutamine in the cell culture media that in turn leads to a more alkaline podocyte cytosol.
Figure 3C:
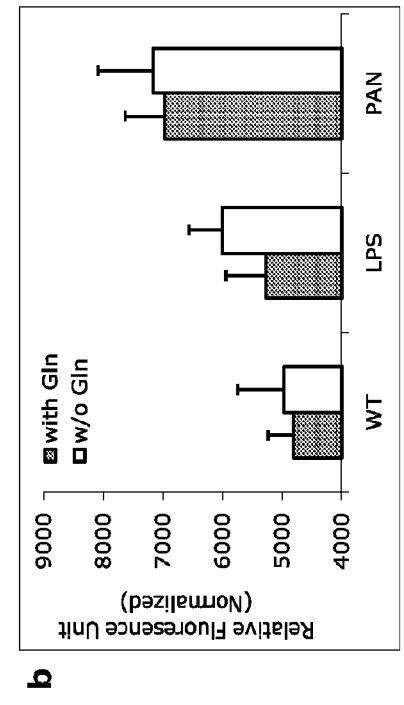

Podocyte pH was assessed with CMFDA—an indicator for pH. Higher green signal is consistent with a more alkaline cell. The presence of high glutamine levels in cell culture media alkalinizes the normal podocytes as well as podocytes that lack integrin α3β1 (genetic model cells for podocyte disease) (FIG. 3A). Both, LPS and PAN treatment stimulate cathepsin L activity in podocytes. Cathepsin L activity is lower in the presence of high glutamine in the cell culture media that in turn leads to a more alkaline podocyte cytosol (FIGS. 3B, 3C).

Figures 4A, 4B, 4C:
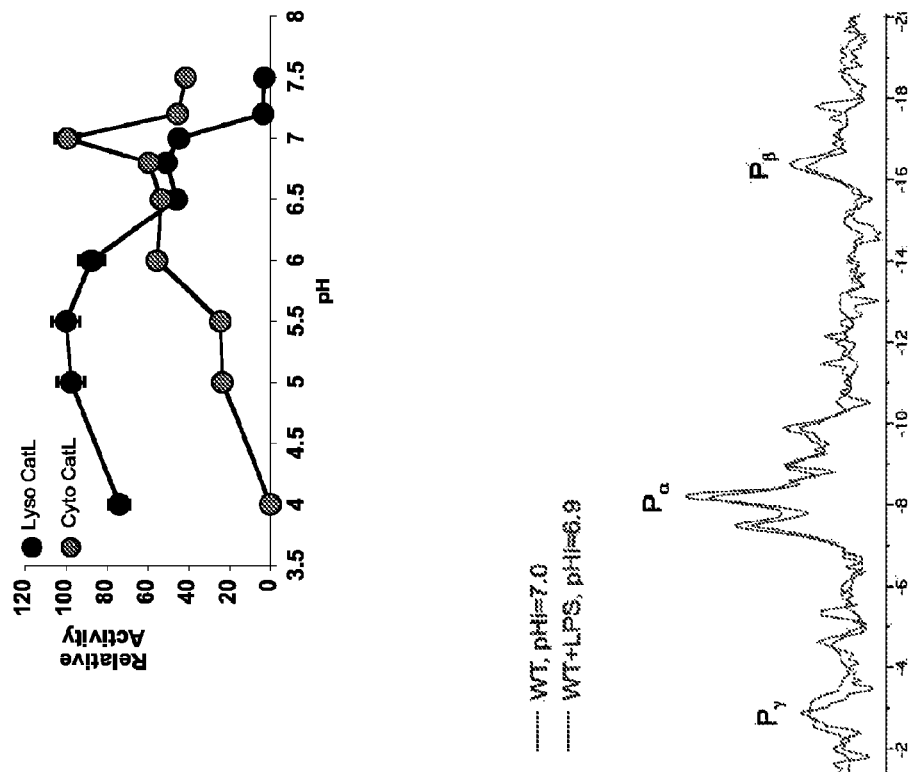
FIG. 4A: Cytosolic extracts were probed for cathepsin L activity harvested from podocytes that lack CD2AP. Lack of CD2AP stimulates cytosolic cathepsin L expression and activity. The data shows strong activity of cathepsin L at pH 7.0.
FIG. 4B: Comparison of cytosolic and lysosomal cathepsin L activity with respect to pH. Cytosolic cathepsin L is most active at pH 7.2 whereas lysosomal cathepsin L at pH 5.
FIG. 4C: NMR spectra analysis of podocyte cytosolic lysates form normal and LPS-stimulated podocytes. The cytosolic pH of podocytes is 7.0 and 6.9 after LPS stimulus.

FIG. 4A shows cytosolic extracts probed for cathepsin L activity harvested from podocytes that lack CD2AP. Lack of CD2AP stimulates cytosolic cathepsin L expression and activity. The data shows strong activity of cathepsin L at pH 7.0. FIG. 4B shows the comparison of cytosolic and lysosomal cathepsin L activity with respect to pH. Cytosolic cathepsin L is most active at pH 7.2 whereas lysosomal cathepsin L at pH 5. FIG. 4C shows the NMR spectra analysis of podocyte cytosolic lysates from normal and LPS-stimulated podocytes. The cytosolic pH of podocytes is 7.0 and 6.9 after LPS stimulus.

Figure 5A:
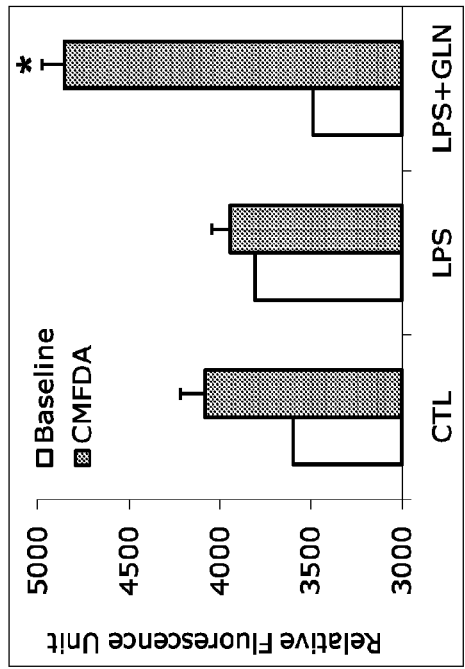
FIG. 5A: Pretreatment of mice with glutamine injection ameliorates LPS mediated proteinuria.
Figure 5B:
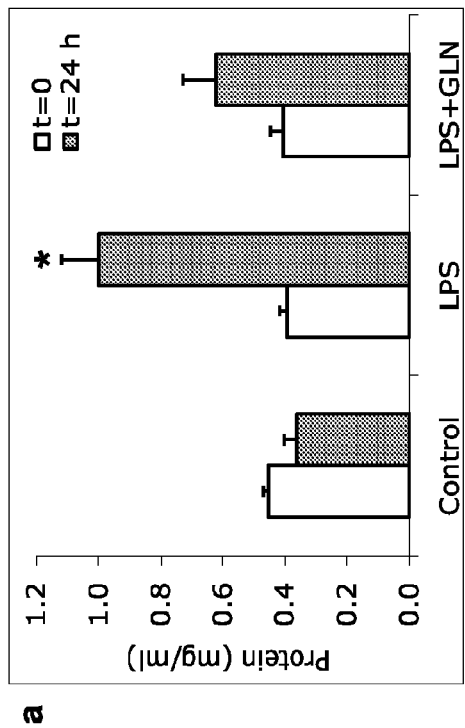
FIG. 5B: Glutamine injections are associated with increase in CMFDA fluorescence after LPS stimulation in mice, showing an increase in glomerular pH.
Figure 5C:
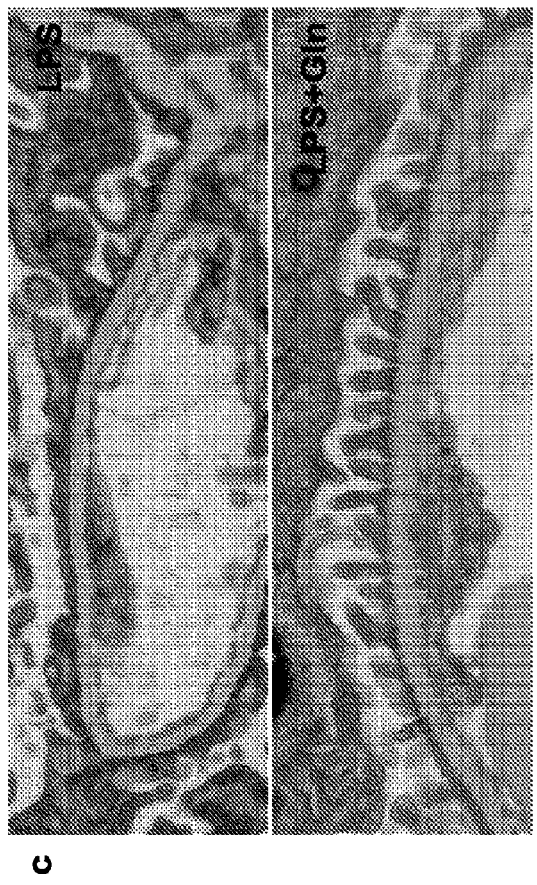
FIG. 5C: Glutamine pre-load in mice protects podocytes from foot process effacement.

FIG. 5A shows that pretreatment of mice with glutamine injection ameliorates LPS mediated proteinuria. FIG. 5B shows that glutamine injections are associated with increase in CMFDA fluorescence after LPS stimulation in mice, showing an increase in glomerular pH. FIG. 5C shows that glutamine pre-load in mice protects podocytes from foot process effacement.

Figure 6:
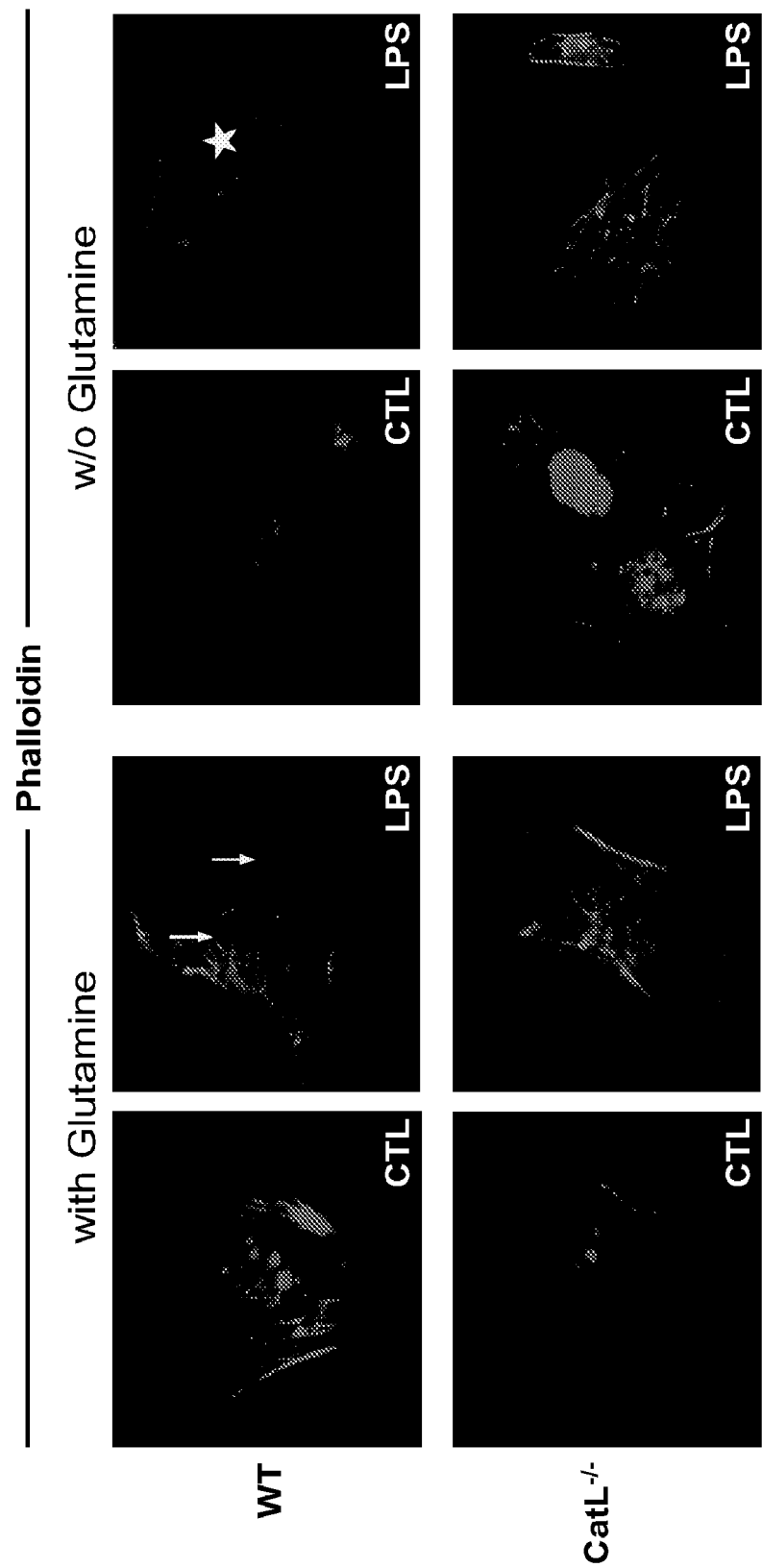
FIG. 6 shows that the actin cytoskeleton of podocytes is regulated by cathepsin L. Presence of glutamine in cell culture media improves F-actin presence in cultured wt podocytes after LPS treatment (arrows) when compared to wt podocytes grown in the absence of glutamine (star). The absence of cathepsin L protects from LPS-mediated loss of F-actin.

The actin cytoskeleton of podocytes is regulated by cathepsin L. Presence of glutamine in cell culture media improved F-actin presence in cultured wt podocytes after LPS treatment (arrows) when compared to wt podocytes grown in the absence of glutamine (star) (FIG. 6). The absence of cathepsin L protected from LPS-mediated loss of F-actin.

Figure 7:
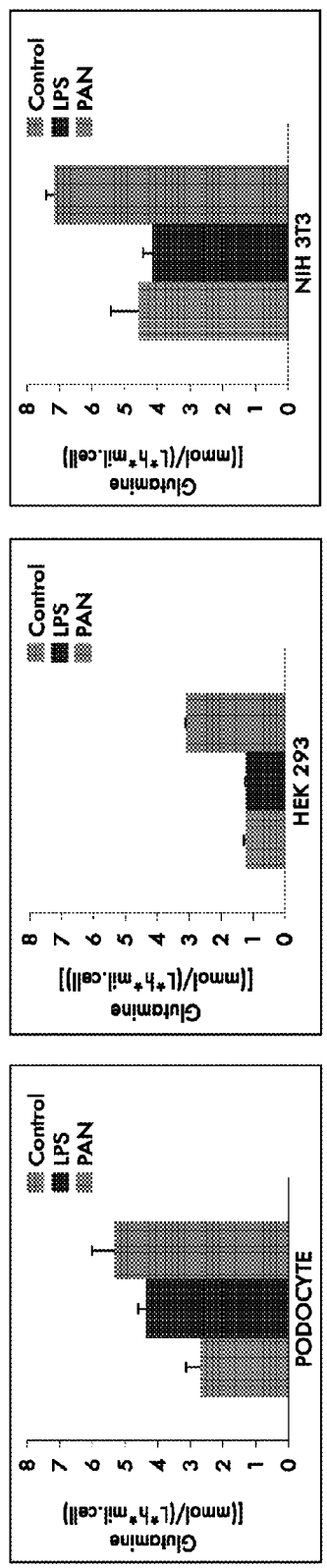
FIG. 7 shows that the glutamine uptake rates in podocytes are stimulated by LPS as well as by PAN. Other mammalian cells (HEK293 and NIH 3T3) did not respond to LPS but to PAN in increasing glutamine uptake rate.

FIG. 7 shows the glutamine uptake rates in podocytes which were stimulated by LPS as well as by PAN. Other mammalian cells (HEK293 and NIH 3T3) did not respond to LPS but to PAN in increasing glutamine uptake rate.

Figure 8:
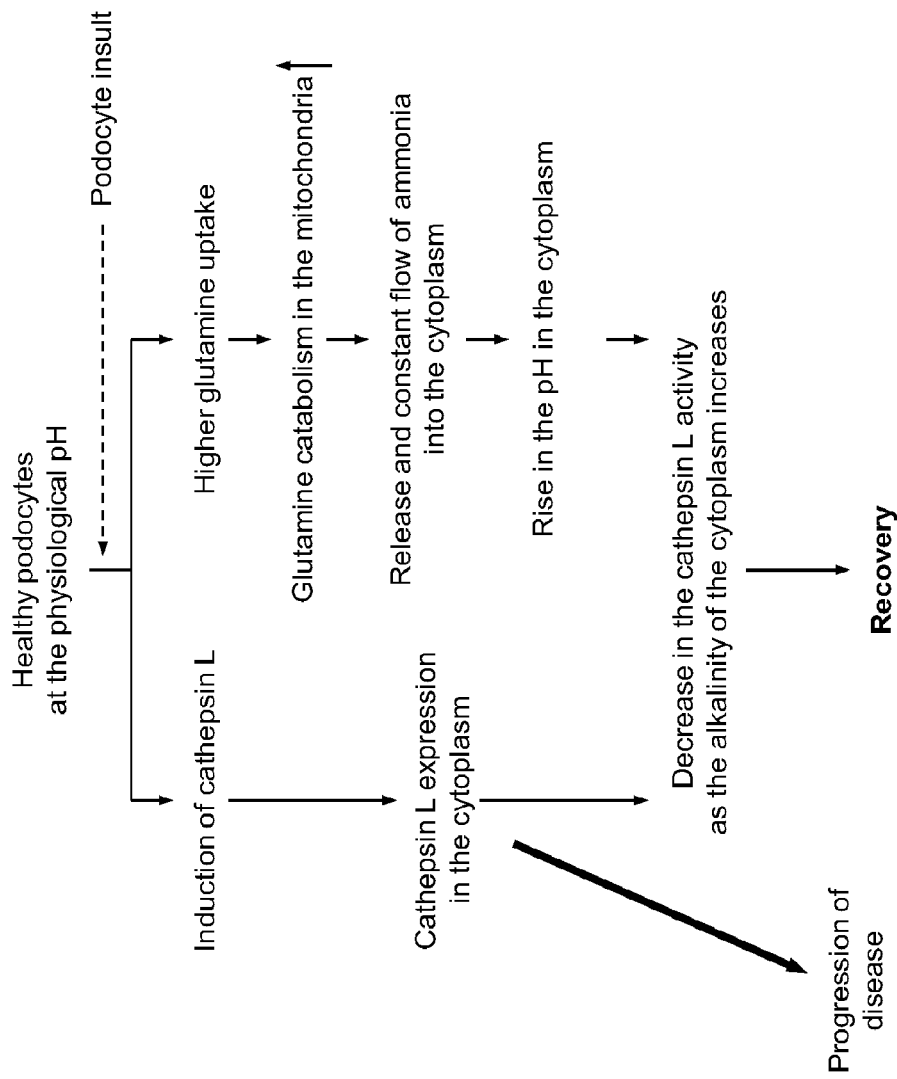
FIG. 8 is a schematic outlining the buffering of induced cathepsin L activity during podocyte disease by adjusting the podocyte pH. Podocyte injury is coupled to an increase in glutamine in part by increasing expression of SNAT proteins. Increased glutamine affects mitochondrial function and increases podocyte pH. A more alkaline pH helps to limit the disease causing action of cytosolic cathepsin L facilitating cellular recovery. Persistent elevated levels of cytosolic cathepsin L expression/activity can drive more severe disease progression.
Figure 9:
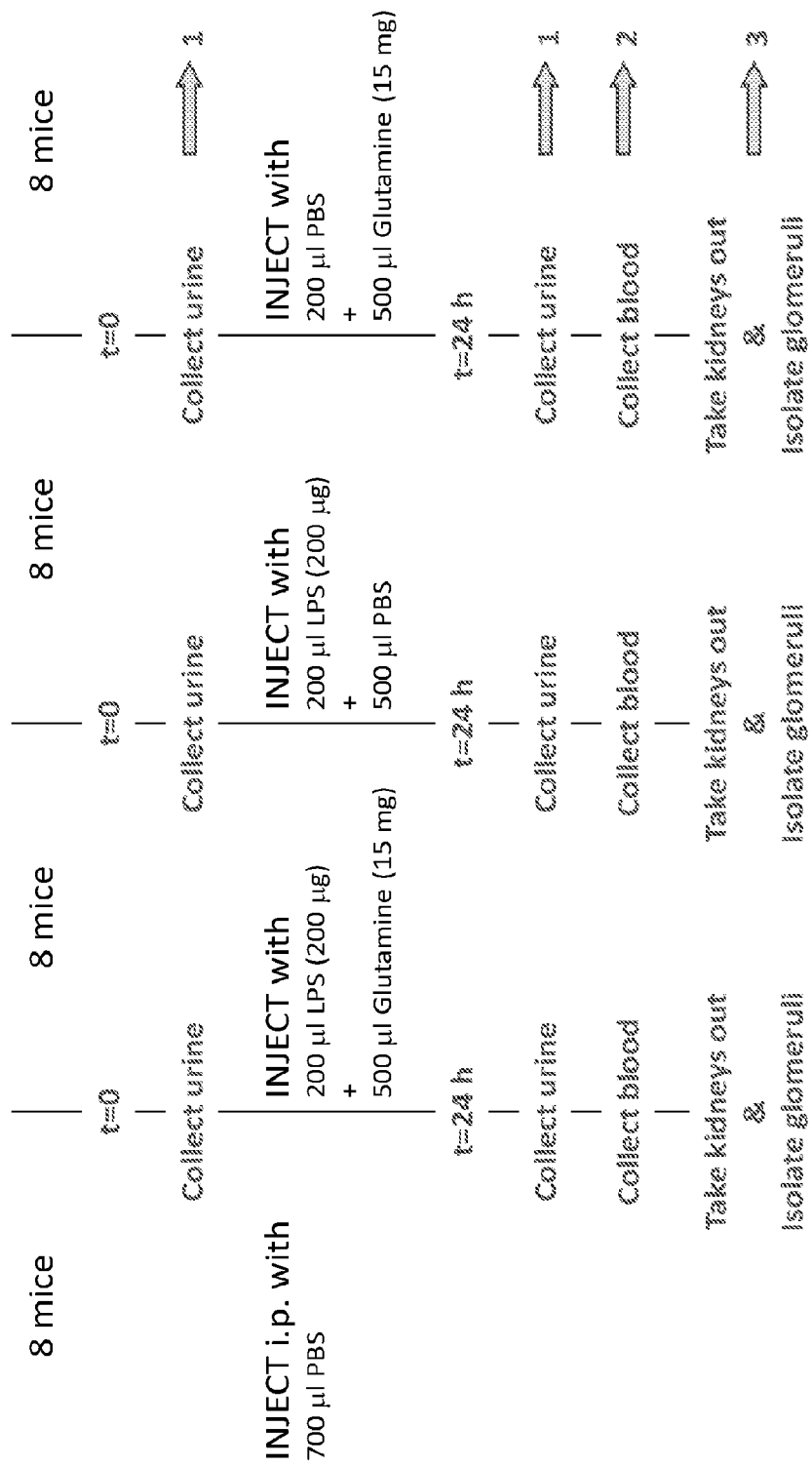
FIG. 9 is a schematic showing the experimental protocol used for glutamine injection in mice.

FIG. 8 is a schematic outlining the buffering of induced cathepsin L activity during podocyte disease by adjusting the podocyte pH. Podocyte injury is coupled to an increase in glutamine in part by increasing expression of SNAT proteins. Increased glutamine affects mitochondrial function and increases podocyte pH. A more alkaline pH helps to limit the disease causing action of cytosolic cathepsin L facilitating cellular recovery. Persistent elevated levels of cytosolic cathepsin L expression/activity can drive more severe disease progression.

Example 2

Reduction of Proteinuria Through Podocyte Alkalinization

Podocytes are highly differentiated cells and critical elements for the filtration barrier of the kidney. Loss of their foot process architecture results in urinary protein loss, a hallmark of kidney disease. Here we show a novel role for the neutral aminoacid glutamine in structural and functional regulation of the kidney filtration barrier. Metabolic flux analysis of cultured podocytes using genetic, toxic and immunologic injury models identified increased glutamine utilization pathways. We show that glutamine uptake is increased in diseased podocytes to couple nutrient support to increased demand during the disease state. This feature can be utilized to transport increased amounts of glutamine into damaged podocytes. The consequences are alkalinization of the podocyte cytosol and reduction of cytosolic cathepsin L protease activity that all together results in a stable podocyte cytoskeleton and when applied in vivo in a reduction in proteinuria during glomerular injury in mice. In summary our data provides a metabolic opportunity to combat urinary protein loss through modulation of podocyte aminoacid utilization.

Introduction

The central metabolism of a cell can determine its short- and long-term structure and function. When a disease state arises, the metabolism of cells, the overall substrate utilization and production are altered in a way that the cell can survive or adapt under the disease-state physiology. Although the response of cells to injury was studied thoroughly in various model systems, the knowledge regarding the metabolism of disease in eukaryotic cells is still under intense investigation. Recent advances in analytical methods and mathematical tools have led to novel approaches to better define disease pathophysiology utilizing computational biology which relies on the integration of experimentation, data processing and modeling. The attempt to formulate current knowledge in mathematical terms has led to the development of several mathematical modeling tools (i.e., metabolic flux analysis, metabolic control analysis, etc.) that helps to understand an entire biological system from basic structure to dynamic interactions. We have used Metabolic Flux Analysis (MFA) to study the aminoacid metabolism of kidney podocytes under normal and disease conditions. Podocytes are specialized cells within the glomerulus that are essential for ultrafiltration. Glomerular diseases that originate from podocyte dysfunction represent a global health problem and affect some 100 million people worldwide (1). Podocytes form foot processes (FP), highly dynamic cellular extensions that are connected by specialized cell-cell junctions or slit diaphragms (SD) (2). The SD contains numerous proteins important for size and charge selectivity of the kidney filter as well as for signaling events (3). Together with the glomerular basement membrane (GBM) and the glomerular endothelial cells, podocytes form a key component of the kidney permeability barrier (4). Most forms of proteinuria are characterized by a reduction of podocyte membrane extensions and transformation of podocyte FPs into a band of cytoplasm (referred to as FP effacement). The molecular framework and biochemical signals underlying normal podocyte function has been studied with great success elucidating critical podocyte proteins and pathways. In addition to genetic mutations that perturb podocyte function (5), acquired or secondary forms of podocyte damage are more commonly prevalent and can entail the induction of a cytosolic variant of the cysteine protease cathepsin L (6) that in turn cleaves the large GTPase dynamin as well as synaptopodin. Both proteins help control the normal cytoarchitecture of podocytes that controls proper kidney filter function (7, 8). What remains unclear is the metabolism of podocytes during the maintenance and degradation of healthy podocyte structure and how the podocyte metabolism is possibly related to cytoskeletal regulation of the kidney filtration barrier. In this report, we describe the results from a metabolic flux model for podocytes. We applied this model to aminoacid measurements obtained from in vitro models for podocyte injury. We find that glutamine utilization and ammonia production pathways are critically enhanced in diseased podocytes. Since glutamine participates in the regulation of podocyte pH, we manipulated glutamine uptake and found this being a measure to blunt the activity of cytosolic cathepsin L that in turn protects the podocyte. Alkalinized podocytes have less cytoskeletal arrangement and stable synaptopodin protein expression. Mice loaded with glutamine develop less proteinuria in the LPS injury model.

Results

Construction of a podocyte metabolic network model: To define the amino acid metabolism in podocytes we constructed a Metabolic Network Model (FIG. 10a). This moderately detailed model was used as a basis for quantification of the fluxes for cultured podocyte cells. It is based on podocyte mitochondrial proteome expression analysis (9) and podocyte mRNA expression profile (data not shown). This information was combined with metabolic network information previously employed for hybridomas (10), CHO cells (11), 293 HEK cells (12) and hepatocytes (13) as all eukaryotic cells share similar operative metabolic enzyme compositions. In the derived podocyte model, there are 26 intracellular fluxes and 24 fluxes for transport rates and biosynthesis rates that can be measured. The transport fluxes are formally defined for each measured metabolite (8 amino acids, glucose, lactate, ornithine and urea), and each rate is defined with a positive sign for production. Each extracellular metabolite is linked to its intracellular counterpart metabolite pool. Forty-two metabolites (Table 2) constitute the nodes for pseudo steady-state mass balances (Table 1). Intracellular fluxes are overall biochemical reactions representing major metabolic pathways: Glycolysis (flux no.s 1 to 5), reduction of pyruvate to lactate (no. 6), Krebs cycle (no.s 7-14), urea production (no.s 15, 16), amino acid catabolism (no.s 17-23), pentose phosphate pathway (no. 24), oxygen uptake and electron transport (no.s 25, 26). All pathways were verified as feasible using bioinformatic databases (14). The metabolic network was solved using set up of a stoichiometric matrix for the network of reactions occurring in podocytes.

Metabolic Flux Analysis emphasizes glutamine utilization pathways for podocyte function: We utilized cultured normal podocytes (control) (15) and three in vitro models for podocyte damage: i) podocytes with α3 integrin deletion (genetic model) (16); ii) podocytes treated with lipopolysaccharides (LPS, immunological model) (17); and iii) podocytes treated with puromycin aminonucleoside (PAN, toxic model) (18). We studied the metabolism of these podocyte models using Metabolic Flux Analysis (MFA). We performed modeling using MFA that includes eight aminoacids. Using the podocyte MFA network, we were able to extract podocyte aminoacid and glucose utilization (FIG. 10b-d) that was also independently measured in direct validation studies (data not shown). All analyzed modeling and experimentation data supported the notion that the aminoacid metabolism of podocytes is changed in disease. Glutamine metabolism of podocytes in all disease models favor deamination (i.e., removal of an amine group as in flux no. 18, Table 1) rather than transamination pathways (i.e., the transfer of an amine group from one molecule to another as in flux no. 20, Table 1) that are controlled by glutamate dehydrogenase and alanine aminotransferase activities, respectively. Eventually, the ammonia buildup reached higher levels in disease cultures.

We also analyzed glutamine uptake in other mammalian cells (HEK 293 and NIH 3T3) that did not respond to LPS but to PAN in increasing glutamine uptake rate (FIG. 6). All together, these experiments discovered a uniform metabolic response for podocytes that are injured.

Glutaminolysis, ammonia production and the uptake rate of glucogenic amino acids are increased in all disease models: Glutamine is involved in a wide variety of metabolic pathways and plays key roles in many physiological processes in various organs (19, 20). Glutamine is available in human blood as well as in our podocyte medium used for cell culture. We found that podocyte glutamine uptake rate is 1.6 to 2.1 times higher in disease models than the rate in the control cultures (FIG. 10b). This glutamine-avid behavior of injured podocytes is similar to glucose uptake (data not shown) indicating the higher need of substrates under disease conditions. Of note, α3 integrin-KO cells displayed the highest rate of glutamine uptake. Glutaminolysis is related to the glucogenic amino acid uptake (i.e., the uptake rate of all amino acids except leucine and lysine). Therefore, we analyzed glucogenic amino acid uptake rates of all models. In FIG. 10c, the sum of the uptake rates of all glucogenic amino acids except glutamine was analyzed for control (WT) and disease (LPS, PAN, and α3 integrin-KO) models. We observed a similar pattern of increased nutrient utilization highlighting the relevance of glutamine uptake and glutaminolysis.

Another indirect measure of glutaminolysis is ammonia production in the mitochondria. Considering that a glutamine molecule consists of two nitrogen atoms and that each of glutamate, alanine and aspartate molecules contain one nitrogen atom, the nitrogen balance was calculated as the difference between twice the glutamine removed and the sum of glutamate, alanine and aspartate accumulated. These calculations revealed that the amount of nitrogen incorporated by podocytes (mainly from glutamine uptake) exceeded the amount of nitrogen removed as glutamate, alanine and aspartate by 3.4, 6.4, 6.8 and 8.1 $\mu mol \cdot L^{-1, h-1} \cdot (\text{million cells})^{-1}$ in control, immunological, toxic and genetic models, respectively (data not shown). This suggests that a considerable part of nitrogen was released in form of ammonia (calculated and measured), FIG. 10d. In sum, mitochondrial glutamine utilization and metabolism are increased in all analyzed podocyte disease models.

Podocytes induce expression of SNAT glutamine transporters during injury: Having identified increased glutamine uptake and utilization as a signature for diseased podocytes that varies from other non-differentiated eukaryotic cells (FIG. 7), we studied the expression of the expression of system A (SNAT1, 2, 4) and system N(SNAT3, 5, 6) family members of sodium-coupled neutral amino acid transporters in cultured podocytes (FIG. 2a). Glutamine is known to be a favored substrate throughout the family, except for SNAT4 (21). We also studied these transporters in isolated mouse glomeruli (FIG. 2a). All SNATs were expressed besides SNAT5, 3 and 4 were only found at low levels. Interestingly, mice stimulated with LPS increased markedly the expression of SNAT3. SNAT3, formerly known as SN1 (Slc38a3), is known as an antiporter that function in the presence of Na+ and takes up glutamine for the exchange of H+. It is highly expressed on the mRNA and protein level in the kidney during metabolic acidosis and involved in the regulation of acid-base homeostasis (22-24). In cultured podocytes, we also found a prominent induction of SNAT3 after LPS but did not find SNAT4 and 5 (FIG. 2b).

Modification of intracellular pH by glutamine: One of the key feature in podocyte injury that can be found in all three employed cellular podocyte models is the induction of cytosolic cathepsin L that in turn cleaves critical regulators of the podocyte microfilament system resulting in a reorganization of the podocyte actin cytoskeleton and proteinuria (6). In contrast to lysosomal cathepsin L, cytosolic cathepsin L is operating under non-acidic conditions. Since podocytes possess a wide variety of SNAT transporters that are capable to increase cellular glutamine uptake, and glutamine is a known modifier of cellular pH, we next studied if glutamine modulation in the cell culture medium will be affecting the intracellular pH. We used a fluorescent dye CMFDA (5-chloromethylfluorescein diacetate) that captures changes in intracellular pH by alterations in fluorescence (25). The more alkaline the pH, the more green fluorescence is detected (FIGS. 11a-c). Fluorescent ratios were generated and then converted to absolute pHi values using standard calibration nigericin (37), a K+/H+ exchanger ionophore. We found that control podocytes had a more alkaline cytosolic pH in the presence of glutamine than in the absence of this aminoacid (FIG. 11a). The same finding but even more prominent was observed in □3 integrin-KO podocytes that express high levels of SNAT3 (FIG. 2b). Using CMFDA, the pH in control cells was determined at 7.1 and at 7.3 in α3 integrin-KO podocytes. We next examined the pH changes that occurred in glomeruli in response to glutamine loading in normal and LPS-treated mice that have induced expression of SNAT transporters (FIG. 2b). We noted a significant difference in fluorescent index of isolated glomeruli consistent with glomerular alkalinization in LPS-treated mice that received a high dose (0.75 mg/g) of glutamine (FIG. 12b).

Regulation of cytosolic cathepsin L activity by Ph: Having observed an effect of glutamine on the podocyte cytosolic pH, we next studied if the activity of cytosolic cathepsin L is changed in the absence of presence of glutamine. To this end we first analyzed the precise pH of podocytes in the cytosol using NMR spectra-analysis. The podocyte pH was found to be 7.0 under normal conditions and 6.9 after 24 hours of LPS exposure (FIG. 4c). At this neutral pH, cytosolic cathepsin L isolated from soluble podocyte cellular fractions is highly active compared to fractions from isolated lysosomes that mainly contain the non-truncated cathepsin L form that has its pH optimum at pH 4-5 (FIG. 4a, b). Cytosolic cathepsin L is already present in low concentration in the podocyte cytosol and probably involved in physiological turnover of a few specific substrates to regulate a healthy podocyte actin cytoskeleton (6). During glomerular disease, there is a prominent induction of cytosolic cathepsin L expression and activity and a strong effect on the podocyte actin cytoskeleton through cleaving the GTPase dynamin (6) and the actin-associated protein synaptopodin (7). These cleavage events lead to a reduction of the F-actin cytoskeleton in podocytes (6, 7). F-actin stress fibers are usually running in parallel bundles from one edge to the other in crossing the center of the cell. When we studied the F-actin distribution in podocytes in the absence of glutamine, we noted a strong reduction of F-actin (FIG. 6). The glutamine dependent changes in F-actin structures are not present in podocytes that lack cathepsin L again linking the action of glutamine to the activity of cathepsin L in podocytes (FIG. 6). Together, this data shows that glutamine can affect the activity of cytosolic cathepsin L by modulating podocyte pH.

Treatment of mice with glutamine increases podocyte pH and protects from LPS-induced proteinuria: In order to translate our in vitro findings into a kidney disease relevant model, we next utilized the LPS model in mice known to cause podocyte foot process effacement and proteinuria driven by induction of cytosolic cathepsin L (6). To this end, mice were either injected with only LPS or treated with high dose (0.75 mg/g) glutamine injection 10 min after LPS administration. We analyzed the relative alkalinity of glomeruli using isolated glomeruli that were incubated with green CMFDA. Similar to our in vitro findings in cultured podocytes, isolated glomeruli showed increased alkalinity in the group of mice that received LPS and high dose glutamine load (FIG. 12b). We also tested renal function and measured proteinuria in these mice. We found significant lower amounts of urinary protein/creatinine ratio in LPS-treated mice that were glutamine-loaded when compared to LPS treated animals without glutamine supplementation (FIG. 12a). These effects were also visible on an ultrastructural level. We semi-quantitated the morphology of podocyte foot processes and found decreased foot process effacement in mice that received a combination of LPS and glutamine compared to mice that received just LPS (FIG. 12c).

Discussion

In this study, we used metabolic flux analysis of cultured podocytes that mimic podocytes during glomerular kidney disease and characterized their amino acid metabolism. We found podocytes to be very glutamine-avid which provides an unexpected opportunity for this aminoacid in capitalizing on its effects in the podocyte cytosol. Providing large amounts of glutamine to injured podocytes is resulting in stabilizing podocyte cell function, in particular through modification of podocyte pH and associated effects on cytosolic cathepsin L. This opportunity stems from the metabolic pathway regulation in diseased podocytes that is represented by glutamine uptake, nitrogen turnover and ammonia production. Most likely, these metabolic adjustments can be seen as part of stress related pathways activated in podocytes under damaging conditions.

Podocytes are injured in many forms of human and experimental glomerular disease (26-29), including minimal change disease, focal segmental glomerulosclerosis, diabetes mellitus, membranous glomerulopathy, crescentic (rapidly progressive) glomerulonephritis and lupus nephritis. The early events are characterized by alteration in podocyte slit diaphragm and foot process configuration, resulting in foot process effacement and loss of kidney filter integrity with the appearance of protein in the urine. Foot process effacement is driven by a reorganization of the actin cytoskeleton (30). These early changes are potentially fully reversible (31, 32).

The understanding of the central podocyte metabolism during foot process effacement is in its infancy and might harbour important possibilities that can be exploited to help podocyte cells adapt under disease conditions or to improve their structure and viability. One means for characterizing the intracellular metabolism of cultured podocytes under normal and disease conditions is the identification of the flux distributions by MFA as it offers the advantage of simplicity, i.e., it solely relies on the known stoichiometry of a given biochemical reaction network. We used MFA based on a generated podocyte-specific flux map and studied three podocyte in vitro disease models: (i) podocytes with α3 integrin deletion (genetic model, 16), (ii) podocytes treated with lipopolysaccharides (LPS, immunological model, 17), (iii) podocytes treated with puromycin aminonucleoside (PAN, toxic model, 18). The common denominator of all these cell models is the rearrangement of the actin cytoskeleton. Our employed metabolic network model for podocytes is a moderately detailed model, adapted in part from other eukaryotic cells (9) that we use as a basis for quantification of the fluxes for the cultured podocyte cells. This model revealed aminoacid metabolism and in particular glutamine metabolism as a common signature in diseased podocytes. Glutamine transporters are widely expressed in podocytes and upregulated in disease. Overall, our findings in podocytes are consistent with a glutamine-avid state that can be utilized to transport large amounts of glutamine into the cell. The effects of supplemented glutamine are the rise in podocyte pH that in turn reduces the activity of cathepsin L known to play a major pathogenic role in podocytes after LPS or PAN (6) as well as in the absence of α3 integrin (16). Probably the most surprising finding of the study is the protection of podocytes in mice that were loaded with glutamine. Despite the fact that glutamine is the most abundant aminoacid in the blood, supplementation by injection is maximizing the effect on renoprotection. Interestingly, recent papers have provided evidence that alkalinization of blood in chronic kidney disease patients is associated with improved survival and reduction of proteinuria (33). It is possible that this benefit is at least in part from podocyte protection. In support of this hypothesis, there is protection from F-actin rearrangement, reduced foot process effacement and proteinuria in alkalinized podocytes. While it can be envisioned that glutamine might not be the best candidate in alkalinizing podocytes during glomerular disease, our data provides proof of concept that alkalinization of podocytes with amino acids like glutamine is a novel mode of therapeutic area that will require intensified attention. Additional studies will be necessary to further accelerate alternative modes of podocyte pH regulation and to facilitate the discovery of new therapeutic targets, biomarkers, and ultimately refined strategies to prevent and treat glomerular kidney disease.

Methods

Cells, antibodies, and standard techniques: Mouse podocyte cell lines (15) and HEK 293 cells (6) were grown as described previously. NIH 3T3 cells were cultured in Dulbecco's modified Eagle's minimal essential medium (Invitrogen, Carlsbad, Calif.) supplemented with 10% fetal calf serum (Invitrogen) and incubated in a humidified atmosphere of 95% air and 5% $CO_2$ at 37° C. Antibody used for immunostaining are Alexa Fluor 594 phalloidin (Molecular Probes, Eugene, Oreg.). Subcellular fractionation was performed as described previously (6).

Immunohistochemistry and immunoelectron microscopy: For immunofluorescent labeling, sections were washed once with PBS and incubated with blocking solution (2% FCS, 2% BSA, 0.2% fish gelatin) for 30 min at room temperature before further incubation with the primary antibody for 1 h at room temperature. Antigen-antibody complexes were visualized with secondary antibodies conjugated with fluorochromes. Specimens were analyzed using a Zeiss confocal microscope (Germany). Ultrathin sections of the kidneys were examined with a Philips CM10 electron microscope (The Netherlands). The number of podocytic FPs was counted in 10 different areas of representative glomeruli. In each area, the number of FPs was calculated within a distance of 1 μm on the GBM (34).

RT-PCR: We isolated total RNA from murine cultured podocytes and mouse glomeruli using the Trizol reagent (Invitrogen) according to the manufacturer's instructions. cDNA synthesis was performed with SuperScript II Reverse Transcriptase (Invitrogen) using Oligo(dT)$_{12-18}$ oligonucleotide primers according to the manufacturer's instructions. All samples were run in duplicates.

Animals and treatments: All animal studies were performed under protocols approved by the University of Miami animal care and use committee. C57BL/6 mice were obtained from The Jackson Laboratory. The mouse model LPS-induced proteinuria was utilized as previously described (16). Glutamine (Invitrogen) is injected i.p. (0.75 mg/g mouse) 10 min after LPS (10 mg/g mouse) (Sigma Aldrich, St. Louis, Mo.) injection.

Measurement of cathepsin L activity: Cathepsin L activities in cultured podocytes and in glomeruli was measured using CV-CatL detection kit (Biomol, Plymouth Meeting, Pa.) as described in the manufacturer's instructions. The fluorophore cresyl violet [CV-(FR)$_2$] substrate becomes florescent after Cat L cleavage of the attached Phe-Arg groups. This substrate easily penetrates the cell membrane and the membranes of the internal cellular organelles, enabling the detection of cathepsin activity within living podocytes.

Solving the metabolic network by metabolic flux analysis (MFA): MFA starts with setting up a stoichiometric matrix for a network of reactions occurring in the cell. Considering thousands of reactions taking place in the cell, it is obvious that not all of these can be included in the model. A total of 42 biochemical reactions and 26 metabolites are considered (FIG. 10). Then, the mass balance constraints around intracellular metabolites are specified. These constraints identify a series of linear equations of individual reaction fluxes that must be fulfilled to enable steady state criterion. Mathematically, the reaction network and the mass balance constraints can be summarized in the following matrix notation:

$$S \cdot r = \begin{bmatrix} S_{11} & S_{12} & \cdots & S_{1n} \\ \vdots & \vdots & \vdots & \vdots \\ S_{m1} & S_{m2} & \cdots & S_{mn} \end{bmatrix}_{m \times n} \cdot \begin{bmatrix} r_1 \\ \vdots \\ r_n \end{bmatrix}_{n \times 1} = 0 \quad \text{(Eq. 1)}$$

S is the m×n stoichiometry matrix, with m as the number of metabolites, and n as the number of reactions. The vector r represents all the individual fluxes of intracellular and extracellular compounds, FIG. 10. In this equation, $S_{11}$ denotes the stoichiometric coefficient of the first metabolite in the first reaction while $S_{12}$ denotes for the stoichiometric coefficient of the first metabolite in the second reaction, etc. The right hand side of this equation is made equal to zero assuming the cultured podocytes are in metabolic steady state where the intracellular levels of metabolites are constant (34).

By separating r into measured and unknown components, $r^{meas}$ and $r^{calc}$, respectively, and partitioning matrix S into $S^{meas}$ and $S^{calc}$, where they contain the stoichiometric coefficients of measured and unknown reactions (i.e., internal and transport fluxes), respectively, we obtained:

$$S^{calc} \times r^{calc} + S^{meas} \times r^{meas} = 0 \quad \text{(Eq. 2a)}$$

and $$S^{calc} \times r^{calc} = -S^{meas} \times r^{meas} \quad \text{(Eq. 2b)}$$

Because $S^{calc}$ is not a square matrix, i.e., the number of rows is greater than the number of columns, Eq. 2b cannot be solved by simple inversion. One approach was to use the Moore-Penrose pseudo-inverse method (34), in which each side of Eq. 2b is multiplied by the transpose of $S^{calc}$:

$$(S^{calc})^T \times S^{calc} \times r^{calc} = -(S^{calc})^T \times S^{meas} \times r^{meas} \quad \text{(Eq. 3)}$$

The matrix multiplier of $r^{calc}$ (i.e., $(S^{calc})^T \times S^{calc}$) is now invertible, and Eq. 3 is solved:

$$r^{calc} = -((S^{calc})^T \times S^{calc})^{-1} \times (S^{calc})^T \times S^{meas} \times r^{meas} \quad \text{(Eq. 4)}$$

Since the system of linear equations is overdetermined (more equations than unknown fluxes), the calculated fluxes are algebraic solutions to overdetermined linear systems, and thus are analogous to straightline parameters (slope and intercept) determined by linear regression (35, 36). The vector $r^{calc}$ represents the best global fit to the linear system given by Eq. 4, but individual vector elements may not exactly satisfy local constraints, i.e., a flux balance around a particular metabolite may not close completely, similar to the way individual points may not lie on the linearly regressed line found by minimizing the sum of the least-square distances between all of the points and the line (36). All the matrix operations required for solving Eq. 4 were performed by using MATLAB (The Mathworks Inc., Natick, Mass.) and routinely took a few minutes for each measurement set on a DELL Inspiron 600 m laptop computer with an Intel Pentium M processor. The fluxes obtained by Eq. 4 were reported as mM·L$^{-1}$·h$^{-1}$· (million cells)$^{-1}$.

Measurement of intracellular pH by NMR: Eighty to hundred million podocyte cells were harvested and resuspended in 2-2.5 mL of phosphate-free RPMI medium (MP Biomedicals, Solon, Ohio) with 2.0 mM glutamine (Invitrogen) prior to assay. Phosphorous NMR spectra were acquired on a 14 Tesla Bruker Avance NMR spectrometer (Bruker BioSpin, Billerica, Mass.) with a 10 mm broadband observe (BBO) NMR probe. Cell suspensions were placed in 10 mm (OD) glass NMR tubes (Wilmad LabGlass, Buena, N.J.). Samples were maintained at a temperature of 37° C. Spectra were acquired with a recycle delay time of 2 sec and consisted of 1024 averages. Spectra were analyzed using the iNMR software package (Mestrelab Research, Spain). Intracellular pH (pH$_i$) was calculated from the chemical shift difference (d) between the intracellular inorganic phosphate peak (P$_i$) and the primary phosphate of nucleoside phosphates (P$_a$) using Eq. 1:

$$pH_i = 6.82 + \log\left(\frac{d - 11.58}{13.51 - d}\right) \quad \text{(Eq. 5)}$$

This equation was derived from the reference sample containing 5.0 mM Na$_2$HPO$_4$ (RPMI-1640 medium, Gibco, Carlsbad, Calif.) and 10 mM ATP (Sigma, St. Louis, Mo.). The pH was varied from 6.3 to 8.3 and the dependence of the chemical shift difference (d) between the inorganic phosphate peak and the alpha-phosphate peak of ATP (Pa) were fit to obtain the constants of the equation.

Measurement of intracellular pH by a fluorescent probe: Podocytes were differentiated at 37° C. for 14 days (15) and harvested with trypsin. The pelleted cells were rinsed twice with bicarbonate-free Krebs-Hepes buffer (130 mM NaCl, 4.7 mM KCl, 1.2 mM MgSO$_4$, 1.2 mM KH$_2$PO$_4$, 11.7 mM D-glucose, 1.3 mM CaCl$_2$, 10 mM HEPES, pH 7.4) and then were loaded with 2.5 mM green CMFDA (Molecular Probes, Eugene, Oreg.) in the same buffer and incubated for 30 min at 37° C. After dye loading, cells will be rinsed twice with the buffer and resuspended in fresh medium, allowed to recover at 37° C. for 30 min. Then, the cells were rinsed three times with the buffer and distributed evenly (approximately 40,000 cells/well) into an opaque clear bottom 96-well plate. Buffer alone was also loaded for baseline reading and the fluorescence intensity recorded at 1 min intervals for 15 min. A Spectramax M5 multi-well plate reader (Molecular Devices, Sunnyvale, Calif.) was used to measure fluorescence. The wells were alternately excited at 485 and 440 nm and emission collected through a 538 nm filter. Ratios were then converted to absolute pHi values using the calibration procedure with nigericin (37), a K$^+$/H$^+$ exchanger ionophore. It was used to relate the fluorescence to pH value by setting [K$^+$]$_{out}$= [K$^+$]$_{in}$ and pH$_{out}$=pH$_{in}$ by exposing the cells to a depolarizing high phosphate buffer (140 mM KCl, 1.2 mM MgSO$_4$, 1.2 mM KH$_2$PO$_4$, 11.7 mM D-glucose, 1.3 mM CaCl$_2$, 10 mM HEPES) with different pH (6.0 to 8.0) in the presence of 20 µM nigericin (25).

TABLE 1

Glycolysis Pathway

1  Glucose + ATP → Glucose-6-P + ADP
2  Glucose-6-P + ATP → 2 Glyceraldehyde-3-P + ADP
3  Glyceraldehyde-3-P + ADP + Pi + NAD$^+$ ↔ Phosphoenolpyruvate + ATP + NADH + H$^+$ + H$_2$O
4  Phosphoenolpyruvate + ADP → Pyruvate + ATP
5  Pyruvate + CoA + NAD$^+$ → Acetyl-CoA + NADH + CO$_2$ Lactate Metabolism and Tricarboxylic Acid Cycle 6  Lactate + NAD$^+$ ↔ Pyruvate + NADH + H$^+$
7  Pyruvate + ATP + CO$_2$ ↔ Oxaloacetate + ADP + Pi
8  Acetyl-CoA + Oxaloacetate + H$_2$O → Citrate + CoA + H$^+$
9  Citrate + NAD$^+$ ↔ a-Ketoglutarate + NADH + CO$_2$
10 a-Ketoglutarate + NAD$^+$ + CoA → Succinyl-CoA + CO$_2$ + NADH + H$^+$
11 Succinyl-CoA + GDP + Pi ↔ Succinate + CoA + GTP
12 Succinate + FAD ↔ Fumarate + FADH$_2$
13 Fumarate + H$_2$O ↔ Malate
14 Malate + NAD$^+$ ↔ Oxaloacetate + NADH + H$^+$ Urea Production 15 Arginine + H$_2$O → Urea + Ornithine
16 Ornithine + α-Ketoglutarate + NAD → 2 Glutamate + NADH + H+

Amino Acid Catabolism

17 Glutamine + H$_2$O → Glutamate + NH$_4^+$
18 Glutamate + 0.5 NAD$^+$ + 0.5 NADP$^+$ + H$_2$O ↔ a-Ketoglutarate + 0.5 NADH + 0.5 NADPH + NH$_4^+$ + H$^+$
19 Glyceraldehyde-3-P + Glutamate + 2 NAD+ ↔ Serine + α-Ketoglutarate + 2 NADH + 2 H+
20 Pyruvate + Glutamate → Alanine + α-Ketoglutarate
21 Glutamate + ATP + 2 NADPH → Proline + ADP + 2 NADP+ + H2O
22 Oxaloacetate + Glutamate → Aspartate + α-Ketoglutarate
23 Asparagine + H$_2$O → Aspartate + NH$_4^+$ TABLE 1-continued Pentose Phosphate Pathway 24  Glucose-6-P + 12 NADP$^+$ + 7 H$_2$O → 6 CO$_2$ + 12 NADPH + 12 H$^+$ + Pi Oxygen Uptake and Electron Transport 25  NADH + H$^+$ + 0.5 O$_2$ + 3 ADP → NAD$^+$ + H$_2$O + 3 ATP
26  FADH$_2$ + 0.5 O$_2$ + 2 ADP → FAD + H$_2$O + 2 ATP

TABLE 2

Metabolites & Abbreviations & Metabolites used as "input" to the flux analyis

| | | | |
|---|---|---|---|
| 1 | ACO | Acetoacetyl-CoA | − |
| 2 | ADP | ADP | − |
| 3 | ALA | Alanine | + |
| 4 | AMP | AMP | − |
| 5 | ARG | Arginine | + |
| 6 | ASP | Asparagine | + |
| 7 | AST | Aspartate | + |
| 8 | ATP | ATP | − |
| 9 | CIT | Citrate | − |
| 10 | COA | CoA | − |
| 11 | CO2 | CO$_2$ | − |
| 12 | FAD | FAD | − |
| 13 | FAH | FADH$_2$ | − |
| 14 | FUM | Fumarate | − |
| 15 | GDP | GDP | − |
| 16 | GLC | Glucose | + |
| 17 | GLP | Glucose-6-P | − |
| 18 | GLT | Glutamate | + |
| 19 | GLN | Glutamine | + |
| 20 | GAP | Glyceraldehyde-3-P | − |
| 21 | GTP | GTP | − |
| 22 | H | H$^+$ | − |
| 23 | H2O | H$_2$O | − |
| 24 | KTO | a-Ketoglutarate | − |
| 25 | LAC | Lactate | + |
| 26 | MAL | Malate | − |
| 27 | NAD | NAD$^+$ | − |
| 28 | NDH | NADH | − |
| 29 | NDP | NADP$^+$ | − |
| 30 | NPH | NADPH | − |
| 31 | NH4 | NH$_4^+$ | − |
| 32 | O2 | O$_2$ | − |
| 33 | ORN | Ornithine | + |
| 34 | OXA | Oxaloacetate | − |
| 35 | PEP | Phosphoenolpyruvate | − |
| 36 | PI | Pi | − |
| 37 | PRO | Proline | + |
| 38 | PYR | Pyruvate | − |
| 39 | SER | Serine | + |
| 40 | SUC | Succinate | − |
| 41 | SCA | Succinyl-CoA | − |
| 42 | URE | Urea | + |

REFERENCES

1. USRDS, The United States Renal Data System. 2003. *Am J Kidney Dis* 42 (Suppl. 5), 1-230.
2. Reiser J, Kriz W, Kretzler M, Mundel P. 2000. The glomerular slit diaphragm is a modified adherens junction. *J Am Soc Nephrol* 11:1-8.
3. Benzing T. 2004. Signaling at the slit diaphragm. *J Am Soc Nephrol* 15:1382-1391.
4. Mundel P, Kriz W. 1995. Structure and function of podocytes: An update. *Anal Embryol* 192:385-397.
5. Tryggvason K, Patrakka J, Wartiovaara J. 2006. Hereditary proteinuria syndromes and mechanisms of proteinuria. *N Engl J Med* 354:1387-1401.
6. Sever S, Altintas M M, Nankoe S R, Moeller C C, Ko D, Wei C, Henderson J, del Re E, Kretzler M, Cohen C D, Erickson A, Kerjaschki D, Rudensky A, Nikolic B, Reiser J. 2007. Processing of the GTPase dynamin by extralysosomal cathepsin L defines a mechanism for proteinuric kidney disease. *J Clin Invest* 117:2095-104.
7. Faul C, Donnelly M, Merscher-Gomez S, Chang Y H, Franz S, Delfgaauw J, Chang J M, Choi H Y, Campbell K N, Kim K, Reiser J, Mundel P. 2008. The actin cytoskeleton of kidney podocytes is a direct target of the antiproteinuric effect of cyclosporine A. *Nat Med* 14:931-938.
8. Yanagida-Asanuma E, Asanuma K, Kim K, Donnelly M, Young Choi H, Hyung Chang J, Suetsugu S, Tomino Y, Takenawa T, Faul C, Mundel P. 2006. Synaptopodin orchestrates actin organization and cell motility via regulation of RhoA signalling. *Nat Cell Biol* 8:485-491.
9. Altintas M M, Ulgen K O, Palmer-Toy D E, Shih V E, Kompala D S, Reiser J. 2008. Emerging roles for metabolic engineering: Understanding primitive and complex metabolic models and their relevance to healthy and diseased kidney podocytes. *Curr Chem Biol* 2:68-82.
10. Bonarius H P J, Hatzimanikatis V, Meesters K P H, de Gooijer C D, Schmid G, Tramper J. 1996. Metabolic flux analysis of hybridoma cells in different culture media using mass balances. *Biotechnol Bioeng* 50:299-318.
11. Nyberg G B, Balcarcel R P, Follstad B D, Stephanopoulos G, Wang D I C. 1999. Metabolism of peptide amino acids by chinese hamster ovary cells grown in a complex medium. *Biotechnol Bioeng* 62:324-335.
12. Nadeau I, Sabatie J, Koehl M, Perrier M, Kamen A. 2000. Human 293 cell metabolism in low glutamine-supplied culture: Interpretation of metabolic changes through metabolic flux analysis. *Metab Eng* 2:277-292.
13. Chan C, Berthiaume F, Lee K, Yarmush M L. 2003. Metabolic flux analysis of cultured hepatocytes exposed to plasma. *Biotechnol Bioeng* 81:33-49.
14. Karp P D, Riley M, Saier M, Paulsen I T, Paley S M, Pellegrini-Toole A. 2000. The EcoCyc and MetaCyc databases. *Nucl Acids Res* 28:56-59.
15. Mundel P, Reiser J, Zuniga-Meja Borja A, Pavenstadt H, Davidson G R, Kriz W, Zeller R. 1997. Rearrangements of the cytoskeleton and cell contacts induce process formation during differentiation of conditionally immortalized mouse podocyte cell lines. *Exp Cell Res* 236:248-258.
16. Reiser J, Oh J, Shirato I, Asanuma K, Hug A, Mundel T M, Honey K, Ishidoh K, Kominami E, Kreidberg J A, Tomino Y, Mundel P. 2004. Podocyte migration during nephrotic syndrome requires a coordinated interplay between cathepsin L and alpha3 integrin. *J Biol Chem* 279:34827-34832.
17. Reiser J, Von Gersdorff G, Loos M, Oh J, Asanuma K, Giardino L, Rastaldi M P, Calvaresi N, Watanabe H, Schwarz K, Faul C, Kretzler M, Davidson A, Sugimoto H, Kalluri R, Sharpe A H, Kreidberg J A, Mundel. 2004. Induction of B7-1 in podocytes is associated with nephrotic syndrome. *J Clin Invest* 113:1390-1397.
18. Reiser J, Pixley F J, Hug A, Kriz W, Smoyer W E, Stanley E R, Mundel P. 2000. Regulation of mouse podocyte process dynamics by protein tyrosine phosphatases. *Kidney Int* 57:2035-2042.
19. Stumvoll M, Perriello G, Meyer C, Gerich J. 1999. Role of glutamine in human carbohydrate metabolism in kidney and other tissues. *Kidney Int* 55:778-792.
20. Welbourne T, Routh R, Yudkoff M, Nissim I. 2001. The glutamine/glutamate couplet and cellular function. *News Physiol Sci* 16:157-160.
21. Mackenzie B, Erickson J D. 2004. Sodium-coupled neutral amino acid (System N/A) transporters of the SLC38 gene family. *Pflugers Arch* 447:784-795.

22. Karinch A M, Lin C M, Meng Q, Pan M, Souba W W. 2007. Glucocorticoids have a role in renal cortical expression of the SNAT3 glutamine transporter during chronic metabolic acidosis. *Am J Physiol Renal Physiol* 292:F448-F455.
23. Moret C, Dave M H, Schulz N, Jiang J X, Verrey F, Wagner C A. 2007. Regulation of renal amino acid transporters during metabolic acidosis. *Am J Physiol Renal Physiol* 292:F555-F566.
24. Nowik M, Lecca M R, Velic A, Rehrauer H, Brandli A W, Wagner C A. 2008. Genome-wide gene expression profiling reveals renal genes regulated during metabolic acidosis. Physiol Genomics 32:322-334.
25. Salvi A, Quillan J M, Sadee W. 2002. Monitoring intracellular pH changes in response to osmotic stress and membrane transport activity using 5-chloromethylfluorescein. *AAPS PharmSci* 4:E21.
26. Eddy A A, Schnaper, H W. 1998. The nephrotic syndrome: From the simple to the complex. *Semin Nephrol* 18:304-316.
27. Kriz W, Lemley K V. 1999. The role of the podocyte in glomerulosclerosis. *Curr Opin Nephrol Hyperlens* 8:489-497.
28. Somlo S, Mundel P. 2000. Getting a foothold in nephrotic syndrome. *Nat Genet* 24:333-335.
29. Endlich K, Kriz W, Witzgall R. 2001. Update in podocyte biology. *Curr Opin Nephrol Hypertens* 10:331-340.
30. Shirato I, Sakai T, Kimura K, Tomino Y, Kriz W (1996) Cytoskeletal changes in podocytes associated with foot process effacement in Masugi nephritis. *Am J Pathol* 148:1283-1296.
31. Smoyer W E, Mundel P. 1998. Regulation of podocyte structure during the development of nephrotic syndrome. *J Mol Med* 76:172-183.
32. Reiser, J., Von Gersdorff, G., Simons, M., Schwarz, K., Faul, C., Giardino, L., Heider, T., Loos, M., and Mundel, P. 2002. Novel concepts in understanding and management of glomerular proteinuria. *Nephrol Dial Transplant* 17:951-955.
33. Kovesdy C P, Kalantar-Zadeh K. 2010. Oral bicarbonate: Renoprotective in CKD? *Nat Rev Nephrol* 6:15-7.
34. Lindskog A, Ebefors K, Johansson M E, Stefánsson B, Granqvist A, Arnadottir M, Berg A L, Nyström J, Haraldsson B. 2010. Melanocortin 1 receptor agonists reduce proteinuria. *J Am Soc Nephrol* 21:1290-1298
35. Stephanopoulos G, Aristidou A A, Nielsen J. 1998. Metabolic engineering: Principles and methodologies. Academic Press, San Diego.
36. Arai K, Lee K, Berthiaume F, Tompkins R G, Yarmush M L. 2001. Intrahepatic amino acid and glucose metabolism in a D-galactosamine-induced rat liver failure model. *Hepatology* 34:360-371.
37. Grant R L, Acosta D. 1997. Ratiometric measurement of intracellular pH of cultured cells with BCECF in a fluorescence multi-well plate reader. *In Vitro Cell Dev Biol Anim* 33:256-260.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of treating proteinuria caused by podocyte cytosolic cathepsin L proteolytic activity, comprising:
    administering to a patient having proteinuria caused by podocyte cytosolic cathepsin L proteolytic activity glutamine or a small molecule agent that directly increases podocyte glutamine uptake pH in an amount effective to increase the intra-podocyte pH of the patient to a pH of greater than 7.0 in vivo, to treat the proteinuria caused by podocyte cytosolic cathepsin L proteolytic activity.

2. The method of claim 1, wherein the glutamine or the small molecule agent increases the intra-podocyte pH to a pH of at least 7.5 in vivo.

3. The method of claim 1, wherein administration of the glutamine or the small molecule agent decreases proteinuria by at least 20% as compared to a baseline proteinuria value.

4. The method of claim 1, comprising identifying the patient as having proteinuria by measuring protein concentrations in urine.

5. The method of claim 1, wherein administration of the glutamine or the small molecule agent decreases proteinuria by at least 50% as compared to a baseline proteinuria value.

6. The method of claim 1, wherein the agent is glutamine.

7. The method of claim 1, wherein the proteinuria is caused by a condition selected from the group consisting of: glomerular diseases, membranous glomerulonephritis, focal segmental glomerulonephritis, minimal change disease, nephrotic syndromes, pre-eclampsia, eclampsia, kidney lesions, collagen vascular diseases, stress, strenuous exercise, benign orthostatic (postural) proteinuria, focal segmental glomerulosclerosis (FSGS), IgA nephropathy, IgM nephropathy, membranoproliferative glomerulonephritis, membranous nephropathy, sarcoidosis, Alport's syndrome, diabetes mellitus, kidney damage due to drugs, Fabry's disease, infections, aminoaciduria, Fanconi syndrome, hypertensive nephrosclerosis, interstitial nephritis, Sickle cell disease, hemoglobinuria, multiple myeloma, myoglobinuria, Wegener's Granulomatosis, and Glycogen Storage Disease Type 1.

8. A method of treating progression of renal disease caused by podocyte cytosolic cathepsin L proteolytic activity, comprising:
    administering to a patient having renal disease glutamine or a small molecule agent that directly increases podocyte glutamine uptake in an amount effective to increase intra-podocyte pH of the patient to a pH greater than 7.0 in vivo, to treat progression of renal disease caused by podocyte cytosolic cathepsin L proteolytic activity.

9. The method of claim 8, wherein the glutamine or the small molecule agent increases the intra-podocyte pH to a pH of at least 7.5.

10. The method of claim 8, wherein administration of the glutamine or the small molecule agent treats progression of renal disease by at least 20% compared to a baseline control.

11. The method of claim 8, wherein abnormal urinary protein concentrations as compared to baseline controls are diagnostic or prognostic of the renal disease caused by podocyte cathepsin L activity.

12. The method of claim 8, wherein glutamine is administered to the patient.

* * * * *

UNITED STATES PATENT AND TRADEMARK OFFICE
CERTIFICATE OF CORRECTION

| | | |
|---|---|---|
| PATENT NO. | : 9,205,135 B2 | Page 1 of 1 |
| APPLICATION NO. | : 13/497451 | |
| DATED | : December 8, 2015 | |
| INVENTOR(S) | : Jochen Reiser | |

It is certified that error appears in the above-identified patent and that said Letters Patent is hereby corrected as shown below:

On the title page

Item (56) Col. 2 (Other Publications), line 12, delete "Eviron." and insert -- Environ. --;

Item (57) Col. 2 (Abstract), line 5, delete "indentified." and insert -- identified. --;

In the claims

In Col. 40, line 11, Claim 1, delete "uptake pH" and insert -- uptake --.

Signed and Sealed this
Twelfth Day of April, 2016

Michelle K. Lee
*Director of the United States Patent and Trademark Office*